(12) United States Patent
Dowling et al.

(10) Patent No.: US 7,064,498 B2
(45) Date of Patent: Jun. 20, 2006

(54) LIGHT-EMITTING DIODE BASED PRODUCTS

(75) Inventors: Kevin J. Dowling, Westford, MA (US); Frederick M. Morgan, Quincy, MA (US); Ihor A. Lys, Boston, MA (US); Michael K. Blackwell, Milton, MA (US); Alfred Ducharme, Tewksbury, MA (US); Ralph Osterhout, San Francisco, CA (US); Colin Piepgras, Salem, MA (US); George C. Mueller, Boston, MA (US); Dawn Geary, Southborough, MA (US)

(73) Assignee: Color Kinetics Incorporated, Boston, MA (US)

( * ) Notice: Subject to any disclaimer, the term of this patent is extended or adjusted under 35 U.S.C. 154(b) by 0 days.

(21) Appl. No.: 09/805,590

(22) Filed: Mar. 13, 2001

(65) Prior Publication Data

US 2003/0214259 A9 Nov. 20, 2003

Related U.S. Application Data

(63) Continuation-in-part of application No. 09/742,017, filed on Dec. 20, 2000, now abandoned, and a continuation-in-part of application No. 09/669,121, filed on Sep. 25, 2000, and a continuation-in-part of application No. 09/626,905, filed on Jul. 27, 2000, which is a continuation of application No. 09/425,770, filed on Oct. 22, 1999, now Pat. No. 6,150,774, and a continuation-in-part of application No. 09/344,699, filed on Jun. 25, 1999, and a continuation-in-part of application No. 09/333,739, filed on Jun. 15, 1999, and a continuation-in-part of application No. 09/215,624, filed on Dec. 17, 1998, now Pat. No. 6,528,954, which is a continuation-in-part of application No. 09/213,607, filed on Dec. 17, 1998, and a continuation-in-part of application No. 09/213,189, filed on Dec. 17, 1998, now Pat. No. 6,459,919, and a continuation-in-part of application No. 09/213,581, filed on Dec. 17, 1998, and a continuation-in-part of application No. 09/213,540, filed on Dec. 17, 1998, now Pat. No. 6,720,745, which is a continuation of application No. 09/213,548, filed on Dec. 17, 1998, now Pat. No. 6,166,496, which is a continuation-in-part of application No. 09/213,537, filed on Dec. 17, 1998, now Pat. No. 6,292,901, and a continuation-in-part of application No. 09/213,659, filed on Dec. 17, 1998, now Pat. No. 6,211,626, which is a continuation of application No. 08/920,156, filed on Aug. 26, 1997, now Pat. No. 6,016,038.

(60) Provisional application No. 60/199,333, filed on Apr. 24, 2000, provisional application No. 60/211,417, filed on Jun. 14, 2000, provisional application No. 60/078,861, filed on Mar. 20, 1998, provisional application No. 60/079,285, filed on Mar. 25, 1998, provisional application No. 60/090,920, filed on Jun. 26, 1998, provisional application No. 60/071,281, filed on Dec. 17, 1997, and provisional application No. 60/068,792, filed on Dec. 24, 1997.

(51) Int. Cl.
*G05F 1/00* (2006.01)
*F21V 33/00* (2006.01)

(52) U.S. Cl. ...................................... 315/291; 362/139
(58) Field of Classification Search ............. 315/209 R, 315/291, 292, 312, 362, DIG. 5; 362/154, 362/184, 234, 253, 139, 152
See application file for complete search history.

(56) References Cited

U.S. PATENT DOCUMENTS 2,909,097 A 10/1959 Alden et al.

(Continued)

FOREIGN PATENT DOCUMENTS

AU 6 267 9 12/1996

(Continued)

OTHER PUBLICATIONS

International Search Report from PCT Application PCT/US01/13151.

(Continued)

*Primary Examiner*—Don Wong
*Assistant Examiner*—Minh Dieu A
(74) *Attorney, Agent, or Firm*—Foley Hoag, LLP

(57) ABSTRACT

High-brightness LEDs, combined with a processor for control, can produce a variety of pleasing effects for display and illumination. A system disclosed herein uses high-brightness, processor-controlled LEDs in combination with diffuse materials to produce color-changing effects. The systems described herein may be usefully employed to bring autonomous color-changing ability and effects to a variety of consumer products and other household items. The system may also include sensors so that the illumination of the LEDs might change in response to environmental conditions or a user input. Additionally, the system may include an interface to a network, so that the illumination of the LEDs may be controlled via the network.

104 Claims, 24 Drawing Sheets

U.S. PATENT DOCUMENTS

| | | | |
|---|---|---|---|
| 3,318,185 A | 5/1967 | Kott | |
| 3,383,503 A | 5/1968 | Montgomery | |
| 3,561,719 A | 2/1971 | Grindle | |
| 3,586,936 A | 6/1971 | McLeroy | |
| 3,595,991 A | 7/1971 | Diller | |
| 3,601,621 A | 8/1971 | Ritchie | |
| 3,624,384 A | 11/1971 | Ledingham et al. | |
| 3,643,088 A | 2/1972 | Osteen et al. | |
| 3,689,758 A | 9/1972 | Power | |
| 3,737,647 A | 6/1973 | Gomi | |
| 3,740,570 A | 6/1973 | Kaelin et al. | |
| 3,746,918 A | 7/1973 | Drucker et al. | |
| 3,787,752 A | 1/1974 | Delay | 315/84.5 |
| 3,805,047 A | 4/1974 | Dockstader | |
| 3,814,926 A | 6/1974 | Frasca | |
| 3,818,216 A | 6/1974 | Larraburu | |
| 3,832,503 A | 8/1974 | Crane | |
| 3,858,086 A | 12/1974 | Anderson et al. | |
| 3,866,035 A | 2/1975 | Richey, Jr. | |
| 3,901,121 A | 8/1975 | Kleiner | |
| 3,909,670 A | 9/1975 | Wakamatsu et al. | |
| 3,924,120 A | 12/1975 | Cox, III | |
| 3,942,065 A | 3/1976 | Russ | 313/500 |
| 3,949,350 A | 4/1976 | Smith | |
| 3,958,885 A | 5/1976 | Stockinger et al. | |
| 3,974,637 A | 8/1976 | Bergey et al. | |
| 4,001,571 A | 1/1977 | Martin | |
| 4,009,381 A | 2/1977 | Schreiber et al. | |
| 4,054,814 A | 10/1977 | Fegley et al. | |
| 4,070,568 A | 1/1978 | Gala | |
| 4,076,976 A | 2/1978 | Fenton | |
| 4,082,395 A | 4/1978 | Donato et al. | |
| 4,096,349 A | 6/1978 | Donato | |
| 4,096,552 A | 6/1978 | Ben-Porat | |
| 4,151,547 A | 4/1979 | Rhoades et al. | 357/81 |
| 4,158,922 A | 6/1979 | Dana, III | |
| 4,179,182 A | 12/1979 | Smith | |
| 4,186,425 A | 1/1980 | Nadimi | |
| 4,237,525 A | 12/1980 | Deter | |
| 4,241,295 A | 12/1980 | Williams, Jr. | |
| 4,267,559 A | 5/1981 | Johnson et al. | 357/81 |
| 4,271,408 A | 6/1981 | Teshima et al. | |
| 4,271,457 A | 6/1981 | Martin | |
| 4,272,689 A | 6/1981 | Crosby et al. | |
| 4,273,999 A | 6/1981 | Pierpoint | |
| 4,296,459 A | 10/1981 | DeLuca | |
| 4,298,869 A | 11/1981 | Okuno | |
| 4,309,743 A | 1/1982 | Martin | |
| 4,329,625 A | 5/1982 | Nishizawa et al. | |
| 4,339,788 A | 7/1982 | White et al. | |
| 4,342,947 A | 8/1982 | Bloyd | |
| 4,367,464 A | 1/1983 | Kurahashi et al. | |
| 4,388,567 A | 6/1983 | Yamazaki et al. | |
| 4,388,589 A | 6/1983 | Molldrem, Jr. | |
| 4,392,187 A | 7/1983 | Bornhorst | |
| 4,394,600 A | 7/1983 | Flannagan | |
| 4,420,711 A | 12/1983 | Takahashi et al. | |
| 4,455,562 A | 6/1984 | Dolan et al. | |
| 4,459,645 A | 7/1984 | Glatter | |
| 4,500,796 A | 2/1985 | Quin | |
| 4,597,033 A | 6/1986 | Meggs et al. | |
| 4,605,882 A | 8/1986 | DeLuca | |
| 4,622,881 A | 11/1986 | Rand | |
| 4,625,152 A | 11/1986 | Nakai | |
| 4,635,052 A | 1/1987 | Aoike et al. | |
| 4,647,217 A | 3/1987 | Havel | |
| 4,654,629 A | 3/1987 | Bezos et al. | |
| 4,654,754 A | 3/1987 | Daszkowski | 361/388 |
| 4,656,398 A | 4/1987 | Michael et al. | |
| 4,668,895 A | 5/1987 | Schneiter | |
| 4,675,575 A | 6/1987 | Smith et al. | |
| 4,682,079 A | 7/1987 | Sanders et al. | |
| 4,686,425 A | 8/1987 | Havel | |
| 4,687,340 A | 8/1987 | Havel | |
| 4,688,154 A | 8/1987 | Nilssen | |
| 4,688,869 A | 8/1987 | Kelly | |
| 4,695,769 A | 9/1987 | Schweickardt | |
| 4,701,669 A | 10/1987 | Head et al. | |
| 4,705,406 A | 11/1987 | Havel | |
| 4,707,141 A | 11/1987 | Havel | |
| 4,719,544 A | 1/1988 | Smith | |
| 4,727,289 A | 2/1988 | Uchida | |
| 4,740,882 A | 4/1988 | Miller | |
| 4,753,148 A | 6/1988 | Johnson | |
| 4,771,274 A | 9/1988 | Havel | |
| 4,777,408 A | 10/1988 | DeLuca | |
| 4,779,172 A | 10/1988 | Jimenez et al. | |
| 4,780,621 A | 10/1988 | Bartleucci et al. | |
| 4,794,383 A | 12/1988 | Havel | |
| 4,802,070 A | 1/1989 | Westmoland | |
| 4,818,072 A | 4/1989 | Mohebban | |
| 4,824,269 A | 4/1989 | Havel | |
| 4,833,542 A | 5/1989 | Hara et al. | |
| 4,837,565 A | 6/1989 | White | |
| 4,843,627 A | 6/1989 | Stebbins | |
| 4,845,481 A * | 7/1989 | Havel | 340/815.45 |
| 4,845,745 A | 7/1989 | Havel | |
| 4,848,009 A | 7/1989 | Rodgers | |
| 4,857,801 A | 8/1989 | Farrell | |
| 4,863,223 A | 9/1989 | Weissenbach et al. | |
| 4,870,325 A | 9/1989 | Kazar | |
| 4,874,320 A | 10/1989 | Freed et al. | |
| 4,887,074 A | 12/1989 | Simon et al. | |
| 4,922,154 A | 5/1990 | Cacoub | |
| 4,929,866 A | 5/1990 | Murata et al. | 313/500 |
| 4,930,052 A | 5/1990 | Beige | |
| 4,934,852 A | 6/1990 | Havel | |
| 4,935,665 A | 6/1990 | Murata | 313/500 |
| 4,947,291 A | 8/1990 | McDermott | |
| 4,962,687 A | 10/1990 | Belliveau et al. | |
| 4,965,561 A * | 10/1990 | Havel | 345/46 |
| 4,973,835 A | 11/1990 | Kurosu et al. | |
| 4,974,119 A | 11/1990 | Martin | 361/386 |
| 4,979,081 A | 12/1990 | Leach et al. | |
| 4,980,806 A | 12/1990 | Taylor et al. | |
| 4,992,704 A | 2/1991 | Stinson | |
| 5,003,227 A | 3/1991 | Nilssen | |
| 5,008,595 A | 4/1991 | Kazar | |
| 5,008,788 A | 4/1991 | Palinkas | |
| 5,010,459 A | 4/1991 | Taylor et al. | |
| 5,018,053 A | 5/1991 | Belknap et al. | |
| 5,027,262 A | 6/1991 | Freed | |
| 5,034,807 A | 7/1991 | Von Kohorn | |
| 5,036,248 A | 7/1991 | McEwan et al. | |
| 5,038,255 A | 8/1991 | Nishihashi et al. | |
| 5,054,778 A | 10/1991 | Maleyko | |
| 5,072,216 A | 12/1991 | Grange | |
| 5,078,039 A | 1/1992 | Tulk et al. | |
| 5,083,063 A | 1/1992 | Brooks | |
| 5,089,748 A | 2/1992 | Ihms | |
| 5,117,338 A | 5/1992 | McCrary | |
| 5,122,733 A | 6/1992 | Havel | |
| 5,126,634 A | 6/1992 | Johnson | |
| 5,128,595 A | 7/1992 | Hara | |
| 5,130,909 A | 7/1992 | Gross | |
| 5,134,387 A * | 7/1992 | Smith et al. | 345/692 |
| 5,136,483 A | 8/1992 | Schoniger et al. | 362/61 |
| 5,142,199 A | 8/1992 | Elwell | |
| 5,143,442 A | 9/1992 | Ishikawa et al. | |
| 5,154,641 A | 10/1992 | McLaughlin | |
| 5,161,879 A | 11/1992 | McDermott | |

| | | | | | |
|---|---|---|---|---|---|
| 5,164,715 A | 11/1992 | Kashiwabara et al. | 5,575,554 A | 11/1996 | Guritz |
| 5,173,839 A | 12/1992 | Metz, Jr. ................... 361/387 | 5,583,349 A | 12/1996 | Norman et al. ............... 257/88 |
| 5,184,114 A | 2/1993 | Brown | 5,583,350 A | 12/1996 | Norman et al. ............... 257/88 |
| 5,194,854 A | 3/1993 | Havel | 5,592,051 A | 1/1997 | Korkala |
| 5,201,578 A | 4/1993 | Westmoland | 5,614,788 A | 3/1997 | Mullins et al. |
| 5,209,560 A | 5/1993 | Taylor et al. | 5,621,282 A * | 4/1997 | Haskell ...................... 307/36 |
| 5,225,765 A | 7/1993 | Callahan et al. | 5,621,603 A | 4/1997 | Adamec et al. |
| 5,226,723 A | 7/1993 | Chen | 5,634,711 A | 6/1997 | Kennedy et al. |
| 5,228,686 A | 7/1993 | Maleyko | 5,636,303 A | 6/1997 | Che et al. |
| 5,235,347 A | 8/1993 | Lee ...................... 346/107 R | 5,640,061 A | 6/1997 | Bornhorst et al. |
| 5,253,149 A | 10/1993 | Ostema et al. | 5,642,129 A | 6/1997 | Zavracky et al. |
| 5,254,910 A | 10/1993 | Yang | 5,653,530 A | 8/1997 | Pittman |
| 5,256,948 A | 10/1993 | Boldin et al. | 5,656,935 A | 8/1997 | Havel |
| 5,262,658 A | 11/1993 | Jankowski ................. 257/467 | 5,671,996 A | 9/1997 | Bos et al. .................. 362/83.1 |
| 5,268,828 A | 12/1993 | Miura | 5,673,059 A | 9/1997 | Zavracky et al. |
| 5,278,542 A | 1/1994 | Smith et al. | 5,684,309 A | 11/1997 | McIntosh et al. |
| 5,279,513 A | 1/1994 | Connelly | 5,688,042 A | 11/1997 | Madadi et al. |
| 5,282,121 A | 1/1994 | Bornhorst et al. | 5,701,058 A | 12/1997 | Roth |
| 5,283,517 A | 2/1994 | Havel | 5,712,650 A | 1/1998 | Barlow |
| 5,287,352 A | 2/1994 | Jackson et al. | 5,721,471 A | 2/1998 | Begemann et al. |
| 5,294,865 A | 3/1994 | Haraden | 5,726,535 A | 3/1998 | Yan |
| 5,298,871 A | 3/1994 | Shimohara | 5,729,076 A | 3/1998 | Yamada et al. ............. 362/235 |
| 5,301,090 A | 4/1994 | Hed | 5,730,013 A | 3/1998 | Huang |
| 5,307,295 A | 4/1994 | Taylor et al. | 5,734,590 A | 3/1998 | Tebbe |
| 5,323,300 A | 6/1994 | McCrary | 5,751,118 A | 5/1998 | Mortimer |
| 5,329,431 A | 7/1994 | Taylor et al. | 5,752,766 A | 5/1998 | Bailey et al. |
| 5,350,977 A | 9/1994 | Hamamoto et al. | 5,769,527 A | 6/1998 | Taylor et al. |
| 5,357,170 A | 10/1994 | Luchaco et al. | 5,782,555 A | 7/1998 | Hochstein ................... 362/373 |
| 5,371,618 A | 12/1994 | Tai et al. | 5,790,329 A | 8/1998 | Klaus et al. |
| 5,374,876 A | 12/1994 | Horibata et al. | 5,791,965 A | 8/1998 | Kim |
| 5,375,043 A | 12/1994 | Tokunaga | 5,803,579 A | 9/1998 | Turnbull et al. |
| 5,381,074 A | 1/1995 | Rudzewicz et al. | 5,808,592 A | 9/1998 | Mizutani et al. .............. 345/83 |
| 5,386,351 A | 1/1995 | Tabor | 5,808,689 A | 9/1998 | Small |
| 5,388,357 A | 2/1995 | Malita | 5,812,105 A | 9/1998 | Van de Ven |
| 5,402,702 A | 4/1995 | Hata | 5,821,695 A | 10/1998 | Vilanilam et al. |
| 5,404,282 A | 4/1995 | Klinke et al. | 5,836,676 A | 11/1998 | Ando et al. |
| 5,406,176 A | 4/1995 | Sugden | 5,838,247 A | 11/1998 | Bladowski |
| 5,408,764 A | 4/1995 | Wut | 5,848,837 A | 12/1998 | Gustafson |
| 5,410,328 A | 4/1995 | Yoksza et al. | 5,850,126 A | 12/1998 | Kanbar |
| 5,412,284 A | 5/1995 | Moore et al. | 5,851,063 A | 12/1998 | Doughty et al. |
| 5,412,552 A | 5/1995 | Fernandes | 5,852,658 A | 12/1998 | Knight et al. |
| 5,420,482 A * | 5/1995 | Phares ...................... 315/292 | 5,854,542 A | 12/1998 | Forbes |
| 5,421,059 A | 6/1995 | Leffers, Jr. | RE36,030 E | 1/1999 | Nadeau |
| 5,432,408 A | 7/1995 | Matsuda et al. | 5,857,767 A | 1/1999 | Hochstein ................... 362/294 |
| 5,436,535 A | 7/1995 | Yang | 5,859,508 A | 1/1999 | Ge et al. |
| 5,436,853 A | 7/1995 | Shimohara | 5,876,109 A | 3/1999 | Scalco |
| 5,437,437 A | 8/1995 | Takano et al. | 5,893,631 A | 4/1999 | Padden |
| 5,450,301 A | 9/1995 | Waltz et al. | 5,894,196 A | 4/1999 | McDermott |
| 5,461,188 A | 10/1995 | Drago et al. | 5,895,986 A | 4/1999 | Walters et al. |
| 5,463,280 A | 10/1995 | Johnson | 5,896,010 A | 4/1999 | Mikolajczak et al. |
| 5,465,144 A | 11/1995 | Parker et al. | 5,907,742 A | 5/1999 | Johnson et al. |
| 5,471,052 A | 11/1995 | Ryczek | 5,912,653 A | 6/1999 | Fitch |
| 5,475,300 A | 12/1995 | Havel | 5,921,652 A | 7/1999 | Parker et al. |
| 5,475,368 A | 12/1995 | Collins | 5,924,784 A * | 7/1999 | Chliwnyj et al. ............. 307/64 |
| 5,477,433 A | 12/1995 | Ohlund | 5,927,845 A | 7/1999 | Gustafson et al. |
| 5,489,827 A | 2/1996 | Xia | 5,938,321 A | 8/1999 | Bos et al. .................. 362/83.1 |
| 5,491,402 A | 2/1996 | Small | 5,946,209 A | 8/1999 | Eckel et al. |
| 5,493,183 A | 2/1996 | Kimball | 5,952,680 A | 9/1999 | Strite |
| 5,497,307 A | 3/1996 | Bae et al. | 5,959,547 A | 9/1999 | Tubel et al. |
| 5,504,395 A | 4/1996 | Johnson et al. | 5,961,201 A | 10/1999 | Gismondi |
| 5,504,664 A | 4/1996 | Ostema | 5,963,185 A | 10/1999 | Havel |
| 5,519,496 A | 5/1996 | Borgert et al. | 5,974,553 A | 10/1999 | Gandar |
| 5,519,591 A | 5/1996 | McCrary | 5,975,717 A | 11/1999 | Rahman |
| 5,528,474 A | 6/1996 | Roney et al. ................ 362/249 | 5,980,064 A | 11/1999 | Metroyanis |
| 5,530,322 A * | 6/1996 | Ference et al. ............. 315/295 | 6,008,783 A | 12/1999 | Kitagawa et al. |
| 5,541,817 A | 7/1996 | Hung | 6,016,038 A * | 1/2000 | Mueller et al. ............... 315/291 |
| 5,545,950 A | 8/1996 | Cho | 6,018,237 A * | 1/2000 | Havel ........................ 324/115 |
| 5,559,681 A | 9/1996 | Duarte | 6,020,825 A | 2/2000 | Chansky et al. |
| 5,561,346 A | 10/1996 | Byrne | 6,025,550 A | 2/2000 | Kato |
| 5,567,037 A | 10/1996 | Ferber | 6,031,343 A | 2/2000 | Recknagel et al. |
| 5,575,459 A | 11/1996 | Anderson | 6,050,695 A | 4/2000 | Fromm |

| | | | | | | |
|---|---|---|---|---|---|---|
| 6,068,383 | A | 5/2000 | Robertson et al. | DE | 03837313 | 5/1989 |
| 6,069,597 | A | 5/2000 | Hansen | DE | 03805998 | 9/1989 |
| 6,072,280 | A | 6/2000 | Allen | DE | 3925767 A1 | 4/1990 |
| 6,086,222 | A | 7/2000 | Juba et al. | DE | 8902905 | 5/1990 |
| 6,092,905 | A | 7/2000 | Koehn | DE | 3917101 | 11/1990 |
| 6,095,661 | A | 8/2000 | Lebens et al. | DE | 3916875 | 12/1990 |
| 6,097,352 | A * | 8/2000 | Zavracky et al. ............ 345/7 | DE | 4041338 A1 | 7/1992 |
| 6,099,185 | A | 8/2000 | Huang et al. | DE | 4130576 C1 | 3/1993 |
| 6,100,913 | A | 8/2000 | Aikoh et al. | DE | 9414688 U1 | 2/1995 |
| 6,111,705 | A | 8/2000 | Rohlfing | DE | 9414689 | 2/1995 |
| 6,116,748 | A | 9/2000 | George | DE | 4419006 A1 | 12/1995 |
| 6,116,751 | A | 9/2000 | Remp | DE | 29607270 U1 | 8/1996 |
| 6,121,944 | A * | 9/2000 | Havel ........................ 345/46 | DE | 19525897 | 10/1996 |
| 6,122,933 | A | 9/2000 | Ohlund | DE | 29620583 U1 | 3/1997 |
| 6,127,783 | A | 10/2000 | Pashley et al. | DE | 19651140 A1 | 6/1997 |
| 6,132,072 | A | 10/2000 | Turnbull et al. | DE | 19602891 A1 | 7/1997 |
| 6,135,604 | A | 10/2000 | Lin | DE | 19602891 | 8/1997 |
| 6,139,172 | A | 10/2000 | Bos et al. .................. 362/494 | EP | 390479 | 3/1990 |
| 6,149,283 | A | 11/2000 | Conway et al. | EP | 507366 | 3/1992 |
| 6,150,771 | A | 11/2000 | Perry | EP | 482680 A1 | 4/1992 |
| 6,150,774 | A | 11/2000 | Mueller et al. | EP | 0495305 A2 | 7/1992 |
| 6,161,910 | A | 12/2000 | Reisenauer et al. | EP | 567280 B1 | 10/1993 |
| 6,166,496 | A | 12/2000 | Lys et al. | EP | 629508 | 6/1994 |
| 6,168,288 | B1 | 1/2001 | St. Claire | EP | 0534710 B1 | 1/1996 |
| 6,175,342 | B1 | 1/2001 | Nicholson et al. | EP | 734082 A2 | 9/1996 |
| 6,181,126 | B1 | 1/2001 | Havel | EP | 0752632 A2 | 1/1997 |
| 6,183,086 | B1 | 2/2001 | Neubert | EP | 0752632 A3 | 8/1997 |
| 6,183,104 | B1 | 2/2001 | Ferrara | EP | 0823812 A2 | 2/1998 |
| 6,184,628 | B1 | 2/2001 | Ruthenberg | EP | 876085 | 4/1998 |
| 6,188,181 | B1 | 2/2001 | Sinha et al. | EP | 0935234 A1 | 8/1999 |
| 6,190,018 | B1 | 2/2001 | Parsons et al. | EP | 0942631 A2 | 9/1999 |
| 6,196,471 | B1 | 3/2001 | Ruthenberg | EP | 1020352 A2 | 7/2000 |
| 6,211,626 | B1 | 4/2001 | Lys et al. | EP | 1113215 A2 | 7/2001 |
| 6,215,409 | B1 | 4/2001 | Blach | EP | 1162400 A2 | 12/2001 |
| 6,220,722 | B1 | 4/2001 | Begemann | FR | 2 640 791 | 6/1990 |
| 6,227,679 | B1 | 5/2001 | Zhang et al. | FR | 88 17359 | 12/1998 |
| 6,233,971 | B1 | 5/2001 | Ohlund | GB | 2045098 A | 10/1980 |
| 6,250,774 | B1 | 6/2001 | Begemann et al. | GB | 2131589 A | 11/1982 |
| 6,252,358 | B1 | 6/2001 | Xydis et al. | GB | 2 135 536 A | 8/1984 |
| 6,252,638 | B1 * | 6/2001 | Johnson et al. ................ 349/5 | GB | 2176042 A | 12/1986 |
| 6,273,338 | B1 | 8/2001 | White | GB | 2210720 A | 6/1989 |
| 6,273,589 | B1 | 8/2001 | Weber et al. | GB | 2 242 364 A | 10/1991 |
| 6,292,901 | B1 | 9/2001 | Lys et al. | GB | 2 244 358 A | 11/1991 |
| 6,296,364 | B1 | 10/2001 | Day et al. | JP | 2247688 | 3/1990 |
| 6,310,590 | B1 | 10/2001 | Havel | JP | 03045166 | 2/1991 |
| 6,323,832 | B1 | 11/2001 | Nishizawa et al. | JP | 6 43830 | 2/1994 |
| 6,329,764 | B1 | 12/2001 | van de Ven | JP | 06043830 | 2/1994 |
| 6,330,111 | B1 | 12/2001 | Myers | JP | 6334223 | 12/1994 |
| 6,331,915 | B1 | 12/2001 | Myers | JP | 7-39120 | 7/1995 |
| 6,340,868 | B1 | 1/2002 | Lys et al. | JP | 7275200 | 10/1995 |
| 6,445,139 | B1 | 9/2002 | Marshall et al. | JP | 8-106264 | 4/1996 |
| 6,448,550 | B1 | 9/2002 | Nishimura | JP | 915840 | 6/1997 |
| 6,459,919 | B1 | 10/2002 | Lys et al. | JP | 9269746 | 10/1997 |
| 6,495,964 | B1 | 12/2002 | Muthu et al. | JP | 9 320766 | 12/1997 |
| 6,498,355 | B1 | 12/2002 | Harrah et al. ................ 257/774 | JP | 10302514 | 11/1998 |
| 6,504,301 | B1 | 1/2003 | Lowery | KR | 1019910009812 | 11/1991 |
| 6,550,949 | B1 * | 4/2003 | Bauer et al. ................ 362/545 | WO | WO 89/05086 | 6/1989 |
| 6,577,287 | B1 | 6/2003 | Havel | WO | WO 94/18809 | 8/1994 |
| 2001/0021109 | A1 | 9/2001 | Schleifer | WO | WO 95/13498 | 5/1995 |
| 2001/0033488 | A1 | 10/2001 | Chliwnyj et al. | WO | 96/11499 | 4/1996 |
| 2002/0047624 | A1 | 4/2002 | Stam et al. | WO | WO 96/41098 | 12/1996 |
| 2003/0107887 | A1 | 6/2003 | Eberl | WO | WO 99/06759 | 2/1999 |
| 2003/0189412 | A1 | 10/2003 | Cunningham | WO | WO 99/30537 A1 | 6/1999 |
| 2004/0066652 | A1 | 4/2004 | Hong | WO | WO 01/73818 A1 | 10/2001 |
| | | | | WO | WO 02/061328 A1 | 8/2002 |

FOREIGN PATENT DOCUMENTS

| | | |
|---|---|---|
| CA | 2 178 432 | 12/1996 |
| CA | 2134848 | 11/1998 |
| DE | 2315709 | 10/1974 |
| DE | 205307 | 12/1983 |
| DE | 3438154 A1 | 4/1986 |

OTHER PUBLICATIONS

Hewlett Packard Components, "Solid State Display and Optoelectronics Designer's Catalog," pp. 30–43, Jul. 1973.

INTEC Research, TRACKSPOT, http://www.intec-research.com/trackspot.htm, pp. 1–4, Apr. 24, 2003.

SHARP, Optoelectronics Data Book, pp. 1096–1097, 1994/1995.

About DMX–512 Lightning Protocol—Pangolin Laser Systems, pp. 1–4, Apr. 7, 2003.

Avitec Licht Design '89–90, pp. 1–4.

Dr. Ing, Ulrich Tietze, Dr. Ing, Christoph Schenk, pp. 566–569.

Furry, Kevin and Somerville, Chuck, Affidavit, LED effects, Feb. 22, 2002, pp. 24–29.

Putnam, Peter H., "The Allure of LED," www.sromagazine.biz, Jun./Jul. 2002, pp. 47–52.

Bremer, Darlene, "LED Advancements Increase Potential," www.ecmag.com, Apr. 2002, p. 115.

Longo, Linda, "LEDS Lead the Way," Home Lighting & Accessories, Jun. 2002, pp. 226–234.

Case No. 6:02–cv–270–ORL–19JGG in the United States District Court, Middle District of Florida, Orlando Division, Plaintiff's Amended Verified Complaint.

Case No. 6:02–cv–270–ORL–19JGG in the United States District Court, Middle District of Florida, Orlando Division, Defendant's Answer and Counterclaims.

Case No. 6:02–cv–270–ORL–19JGG in the United States District Court, Middle District of Florida, Orlando Division, Plaintiff's Answer to Counterclaims.

Case No. 6:02–cv–270–ORL–19JGG in the United States District Court, Middle District of Florida, Orlando Division, Plaintiff's Answers to Defendant's First Set of Interrogatories w/Exhibit 1.

Case No. 02 CV 11137MEL in the United States District Court, District of Massachusetts, Plaintiff's Complaint and Jury Demand.

Case No. 02 CV 11137MEL in the United States District Court, District of Massachusetts, Defendant's Answer and Affirmative Defenses.

"LM117/LM317A/LM317 3–Terminal Adjustable Regulator", National Semiconductor Corporation, May 1997, pp. 1–20.

"DS96177 RS–485 / RS–422 Differential Bus Repeater", National Semiconductor Corporation, Feb. 1996, pp. 1–8.

"DS2003 / DA9667 / DS2004 High Current / Voltage Darlington Drivers", National Semiconductor Corporation, Dec. 1995, pp. 1–8.

"LM140A / LM140 / LM340A / LM7800C Series 3—Terminal Positive Regulators", National Semiconductor Corporation, Jan. 1995, pp. 1–14.

High End Systems, Inc., Trackspot User Manual, Aug. 1997, Excerpts (Cover, Title page, pp. ii through iii and 2–13 through 2–14).

Artistic License, AL4000 DMX512 Processors, Revision 3.4, Jun. 2000, Excerpts (Cover, pp. 7,92 through 102).

Artistic License, Miscellaneous Drawings (3 sheets) Jan. 12, 1995.

Artistic License, Miscellaneous Documents (2 sheets Feb. 1995 and Apr. 1996).

Newnes's Dictionary of Electronics, Fourth Edition, S.W. Amos, et al., Preface to First Edition, pp. 278–279.

"http://www.luminus.cx/projects/chaser", (Nov. 13, 2000), pp. 1–16.

Co–Pending U.S. Appl. No. 09/971,367, filed Oct. 4, 2001, entitled "Multicolored LED Lighting Method and Apparatus," our File No. C01104/70082.

Schlig, Eugene S., "Electrothermal Considerations in Display Applications of Light–Emitting Diodes," *IEEE Transactions on Electron Devices*, vol. ED–19, No. 7, Jul. 1982, pp. 847–851.

Asai, S. et al., "Heat Conductive Wire Matrix Board for Light Emitting Diode (LED) Dot Matrix Display," *Circuit World*, vol. 21, No. 4, 1995, pp. 27–31.

"Cree Research, Inc. Announces Fiscal 1994 Results," *PR Newswire*, Jul. 28, 1994, pp. 1–2.

"Cree Research, Inc. Announces Acquisition of Full–Color LED Display Company," *PR Newswire*, Aug. 9, 1994, pp. 1–2.

Mishiko, Yasuhiro, et al., "Large–Scale Color LED Display System" *National Technical Report*, vol. 33, No. 1, Feb. 1987, pp. 94–101.

Miyoshi, Morimasa et al., "Large–Scale Color LED Stock–Information Display Board,", *National Technical Report*, vol. 33, No. 1, Feb. 1987, pp. 102–107.

Motozono, Takefumi et al., "LED Display Devices," *National Technical Report*, vol. 28, No. 1, Feb. 1982, pp. 74–82.

Tsujikado, Kazumi et al., "Large–Scale LED Display System," *National Technical Report*, vol. 42, No. 3, Jun. 1996, pp. 18–25.

Mishiko, Yasuhiro, et al., "Large–Scale Color LED Display Systemm," *National Technical Report*, vol. 33, No. 1, Feb. 1987, pp. 94–101.

Murata, Kazuhisa, "Developers Continue to Refine Blue LED Technologies for Display Use," *Display Devices*, 1992, Ser. No. 6, pp. 46–50.

Koga, Kazuyuki et al., "RGB Multi–Color LED Dot–Matrix Units and Their Application to Large–Size Flat Displays," *Optoelectronics–Devices and Technologies*, vol. 7, No. 2, pp. 221–229, Dec., 1992.

Murata, Kazuhisa, "SiC Brightens Blues for Full–Color LED Display Units," *Jee*, Nov., 1993, pp. 59–65.

Lerner, Eric. J., "Laser Diodes and LEDs Light Optoelectronics Devices," *Laser Focus World*, Feb., 1997, pp. 109–117.

Martin, David, et al., "Material Advances Light Full–Color LED Displays," *Laser Focus World*, Mar. 1997, pp. 119–124.

* cited by examiner

LIGHT-EMITTING DIODE BASED PRODUCTS

CROSS REFERENCE TO RELATED APPLICATIONS

This application claims the benefit, under 35 U.S.C. §119(e), of the entire disclosure of the following United States provisional patent applications (each of which is incorporated herein by reference):

U.S. Provisional Patent App. No. 60/199,333, filed Apr. 24, 2000; and

U.S. Provisional Patent App. No. 60/211,417, filed Jun. 14, 2000.

This application also claims the benefit as a continuation-in-part of the following United States patent applications:

U.S. patent application Ser. No. 09/215,624, filed Dec. 17, 1998 now U.S. Pat. No. 6,528,954, which is incorporated herein by reference and which claims the benefit of the following provisional applications:

Ser. No. 60/071,281, filed Dec. 17, 1997, entitled "Digitally Controlled Light Emitting Diodes Systems and Methods";

Ser. No. 60/068,792, filed Dec. 24, 1997, entitled "Multi-Color Intelligent Lighting";

Ser. No. 60/078,861, filed Mar. 20, 1998, entitled "Digital Lighting Systems";

Ser. No. 60/079,285, filed Mar. 25, 1998, entitled "System and Method for Controlled Illumination"; and Ser. No. 60/090,920, filed Jun. 26, 1998, entitled "Methods for Software Driven Generation of Multiple Simultaneous High Speed Pulse Width Modulated Signals";

U.S. patent application Ser. No. 09/213,607, filed Dec. 17, 1998;

This application Ser. No. 09/805,590 is a CIP of Ser. No. 09/213,607 ABN and is a CIP of U.S. patent application Ser. No. 09/213,189, filed Dec. 17, 1998, now U.S. Pat. No. 6,459,919, issued Oct. 1, 2002;

CIP of U.S. patent application Ser. No. 09/213,581, filed Dec. 17, 1998;

CIP of U.S. patent application Ser. No. 09/213,540, filed Dec. 17, 1998;

CIP of U.S. patent application Ser. No. 09/333,739, filed Jun. 15, 1999, which is incorporated herein by reference;

CIP of U.S. patent application Ser. No. 09/344,699, filed Jun. 25, 1999, which is incorporated herein by reference;

CIP of U.S. patent application Ser. No. 09/626,905, filed Jul. 27, 2000, now U.S. Pat. No. 6,340,868;

CIP of U.S. patent application Ser. No. 09/669,121 U.S. Pat. No. 6,805,659, filed Sep. 25, 2000, which is incorporated herein by reference and which is a continuation (CON) of U.S. patent application Ser. No. 09/425,770, filed Oct. 22, 1999, now U.S. Pat. No. 6,150,774, issued Nov. 21, 2000, which is a continuation (CON) of U.S. patent application Ser. No. 08/920,156, filed Aug. 26, 1997, now U.S. Pat. No. 6,016,038, issued Jan. 18, 2000;

This application Ser. No. 09/805,590 is a CIP of U.S. patent application Ser. No. 09/742,017, filed Dec. 20, 2000 ABN, which is a continuation (CON) of U.S. patent application Ser. No. 09/213,548, filed Dec. 17, 1998, now U.S. Pat. No. 6,166,496, issued Dec. 26, 2000;

This application Ser. No. 09/805,590 is a CIP of U.S. patent application Ser. No. 09/213,537, filed Dec. 17, 1998, now U.S. Pat. No. 6,292,901, issued Sep. 18, 2001; and is a CIP of U.S. patent application Ser. No. 09/213,659, filed Dec. 17, 1998, now U.S. Pat. No. 6,211,626, issued Apr. 3, 2001.

BACKGROUND OF THE INVENTION

Lighting elements are sometimes used to illuminate a system, such as a consumer product, wearable accessory, novelty item, or the like. Existing illuminated systems, however, are generally only capable of exhibiting fixed illumination with one or more light sources. An existing wearable accessory, for example, might utilize a single white-light bulb as an illumination source, with the white-light shining through a transparent colored material. Such accessories only exhibit an illumination of a single type (a function of the color of the transparent material) or at best, by varying the intensity of the bulb output, a single-colored illumination with some range of controllable brightness. Other existing systems, to provide a wider range of colored illumination, may utilize a combination of differently colored bulbs. Such accessories, however, remain limited to a small number of different colored states, for example, three distinct illumination colors: red (red bulb illuminated); blue (blue bulb illuminated); and purple (both red and blue bulbs illuminated). The ability to blend colors to produce a wide range of differing tones of color is not present Techniques are known for producing multi-colored lighting effects with LED's. Some such techniques are shown in, for example, U.S. Pat. No. 6,016,038, U.S. patent application Ser. No. 09/215,624, and U.S. Pat. No. 6,150,774 the teachings of which are incorporated herein by reference. While these references teach systems for producing lighting effects, they do not address some applications of programmable, multi-colored lighting systems.

For example, many toys, such as balls, may benefit from improved color illumination, processing, and/or networking attributes. There are toy balls that have lighted parts or balls where the entire surface appears to glow, however there is no ball available that employs dynamic color changing effects. Moreover, there is no ball available that responds to data signals provided from a remote source. As another example, ornamental devices are often lit to provide enhanced decorative effects. U.S. Pat. Nos. 6,086,222 and 5,975,717, for example, disclose lighted ornamental icicles with cascading lighted effects. As a significant disadvantage, these systems employ complicated wiring harnesses to achieve dynamic lighting. Other examples of crude dynamic lighting may be found in consumer products ranging from consumer electronics to home illumination (such as night lights) to toys to clothing, and so on.

Thus, there remains a need for existing products to incorporate programmable, multi-colored lighting systems to enhance user experience with sophisticated color changing effects, including systems that operate autonomously and systems that are associated with wired or wireless computer networks.

SUMMARY OF THE INVENTION

High-brightness LEDs, combined with a processor for control, can produce a variety of pleasing effects for display and illumination. A system disclosed herein uses high-brightness, processor-controlled LEDs in combination with diffuse materials to produce color-changing effects. The systems described herein may be usefully employed to bring autonomous color-changing ability and effects to a variety of consumer products and other household items. The system may also include sensors so that the illumination of the LEDs might change in response to environmental conditions or a user input. Additionally, the system may include an interface to a network, so that the illumination of the LEDs may be controlled via the network.

BRIEF DESCRIPTION OF DRAWINGS

The foregoing and other objects and advantages of the invention will be appreciated more fully from the following further description thereof, with reference to the accompanying drawings, wherein.

DETAILED DESCRIPTION OF THE PREFERRED EMBODIMENT(S)

Figure 1:
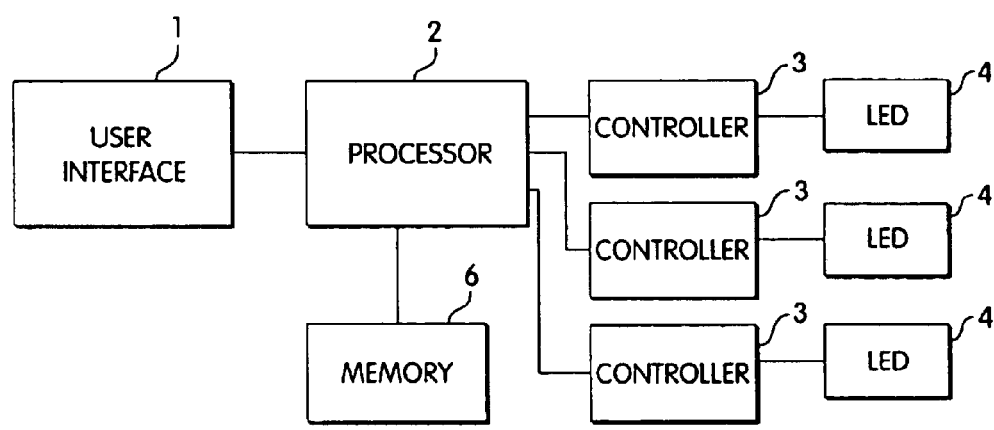
FIG. 1 is a block diagram of a device according to the principles of the invention.

To provide an overall understanding of the invention, certain illustrative embodiments will now be described, including various applications for programmable LED's. However, it will be understood by those of ordinary skill in the art that the methods and systems described herein may be suitably adapted to other environments where programmable lighting may be desired, and that some of the embodiments described herein may be suitable to non-LED based lighting.

As used herein, the term "LED" means any system that is capable of receiving an electrical signal and producing a color of light in response to the signal. Thus, the term "LED" should be understood to include light emitting diodes of all types, light emitting polymers, semiconductor dies that produce light in response to current, organic LEDs, electro-luminescent strips, silicon based structures that emit light, and other such systems. In an embodiment, an "LED" may refer to a single light emitting diode package having multiple semiconductor dies that are individually controlled. It should also be understood that the term "LED" does not restrict the package type of the LED. The term "LED" includes packaged LEDs, non-packaged LEDs, surface mount LEDs, chip on board LEDs and LEDs of all other configurations. The term "LED" also includes LEDs packaged or associated with phosphor wherein the phosphor may convert energy from the LED to a different wavelength.

An LED system is one type of illumination source. As used herein "illumination source" should be understood to include all illumination sources, including LED systems, as well as incandescent sources, including filament lamps, pyro-luminescent sources, such as flames, candle-luminescent sources, such as gas mantles and carbon arch radiation sources, as well as photo-luminescent sources, including gaseous discharges, fluorescent sources, phosphorescence sources, lasers, electro-luminescent sources, such as electro-luminescent lamps, light emitting diodes, and cathode luminescent sources using electronic satiation, as well as miscellaneous luminescent sources including galvano-luminescent sources, crystallo-luminescent sources, kine-luminescent sources, thermo-luminescent sources, triboluminescent sources, sonoluminescent sources, and radioluminescent sources. Illumination sources may also include luminescent polymers capable of producing primary colors.

The term "illuminate" should be understood to refer to the production of a frequency of radiation by an illumination source with the intent to illuminate a space, environment, material, object, or other subject. The term "color" should be understood to refer to any frequency of radiation, or combination of different frequencies, within the visible light spectrum. The term "color," as used herein, should also be understood to encompass frequencies in the infrared and ultraviolet areas of the spectrum, and in other areas of the electromagnetic spectrum where illumination sources may generate radiation.

FIG. 1 is a block diagram of a device according to the principles of the invention. The device may include a user interface 1, a processor 2, one or more controllers 3, one or more LEDs 4, and a memory 6. In general, the processor 2 may execute a program stored in the memory 6 to generate signals that control stimulation of the LEDs 4. The signals may be converted by the controllers 3 into a form suitable for driving the LEDs 4, which may include controlling the current, amplitude, duration, or waveform of the signals impressed on the LEDs 4.

As used herein, the term processor may refer to any system for processing electronic signals. A processor may include a microprocessor, microcontroller, programmable digital signal processor or other programmable device, along with external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. A processor may also, or instead, include an application specific integrated circuit, a programmable gate array, programmable array logic, a programmable logic device, a digital signal processor, an analog-to-digital converter, a digital-to-analog converter, or any other device that may be configured to process electronic signals. In addition, a processor may include discrete circuitry such as passive or active analog components including resistors, capacitors, inductors, transistors, operational amplifiers, and so forth, as well as discrete digital components such as logic components, shift registers, latches, or any other separately packaged chip or other component for realizing a digital function. Any combination of the above circuits and components, whether packaged discretely, as a chip, as a chipset, or as a die, may be suitably adapted to use as a processor as described herein. Where a processor includes a programmable device such as the microprocessor or microcontroller mentioned above, the processor may further include computer executable code that controls operation of the programmable device.

The controller 3 may be a pulse width modulator, pulse amplitude modulator, pulse displacement modulator, resistor ladder, current source, voltage source, voltage ladder, switch, transistor, voltage controller, or other controller. The controller 3 generally regulates the current, voltage and/or power through the LED, in response to signals received from the processor 2. In an embodiment, several LEDs 4 with different spectral output may be used. Each of these colors may be driven through separate controllers 3. The processor 2 and controller 3 may be incorporated into one device, e.g., sharing a single semiconductor package. This device may drive several LEDs 4 in series where it has sufficient power output, or the device may drive single LEDs 4 with a corresponding number of outputs. By controlling the LEDs 4 independently, color mixing can be applied for the creation of lighting effects.

The memory 6 may store algorithms or control programs for controlling the LEDs 4. The memory 6 may also store look-up tables, calibration data, or other values associated with the control signals. The memory 6 may be a read-only memory, programmable memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, address information, and program output or other intermediate or final results. A program, for example, may store control signals to operate several different colored LEDs 4.

A user interface 1 may also be associated with the processor 2. The user interface 1 may be used to select a program from the memory 6, modify a program from the memory 6, modify a program parameter from the memory 6, select an external signal for control of the LEDs 4, initiate a program, or provide other user interface solutions. Several methods of color mixing and pulse width modulation control are disclosed in U.S. Pat. No. 6,016,038 "Multicolored LED Lighting Method and Apparatus", the teachings of which are incorporated by reference herein. The processor 2 can also be addressable to receive programming signals addressed to it.

The '038 patent discloses LED control through a technique known as Pulse-Width Modulation (PWM). This technique can provide, through pulses of varying width, a way to control the intensity of the LED's as seen by the eye. Other techniques are also available for controlling the brightness of LED's and may be used with the invention. By mixing several hues of LED's, many colors can be produced that span a wide gamut of the visible spectrum. Additionally, by varying the relative intensity of LED's over time, a variety of color-changing and intensity varying effects can be produced. Other techniques for controlling the intensity of one or more LEDs are known in the art, and may be usefully employed with the systems described herein. In an embodiment, the processor 2 is a Microchip PIC processor 12C672 that controls LEDs through PWM, and the LEDs 4 are red, green and blue.

Figure 2A:
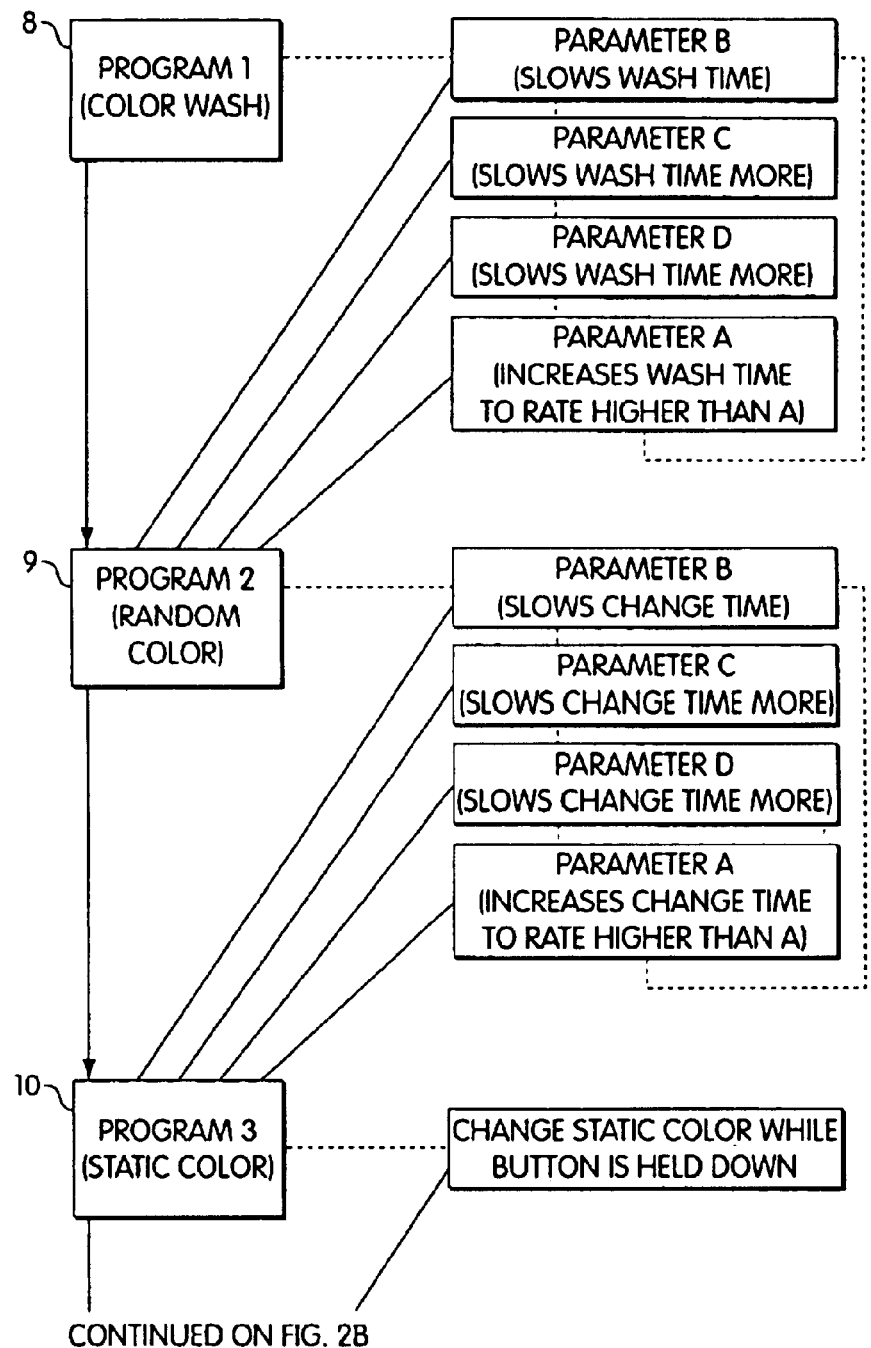
FIGS. 2A–2B are a state diagram showing operation of a device according to the principles of the invention.
Figure 2B:
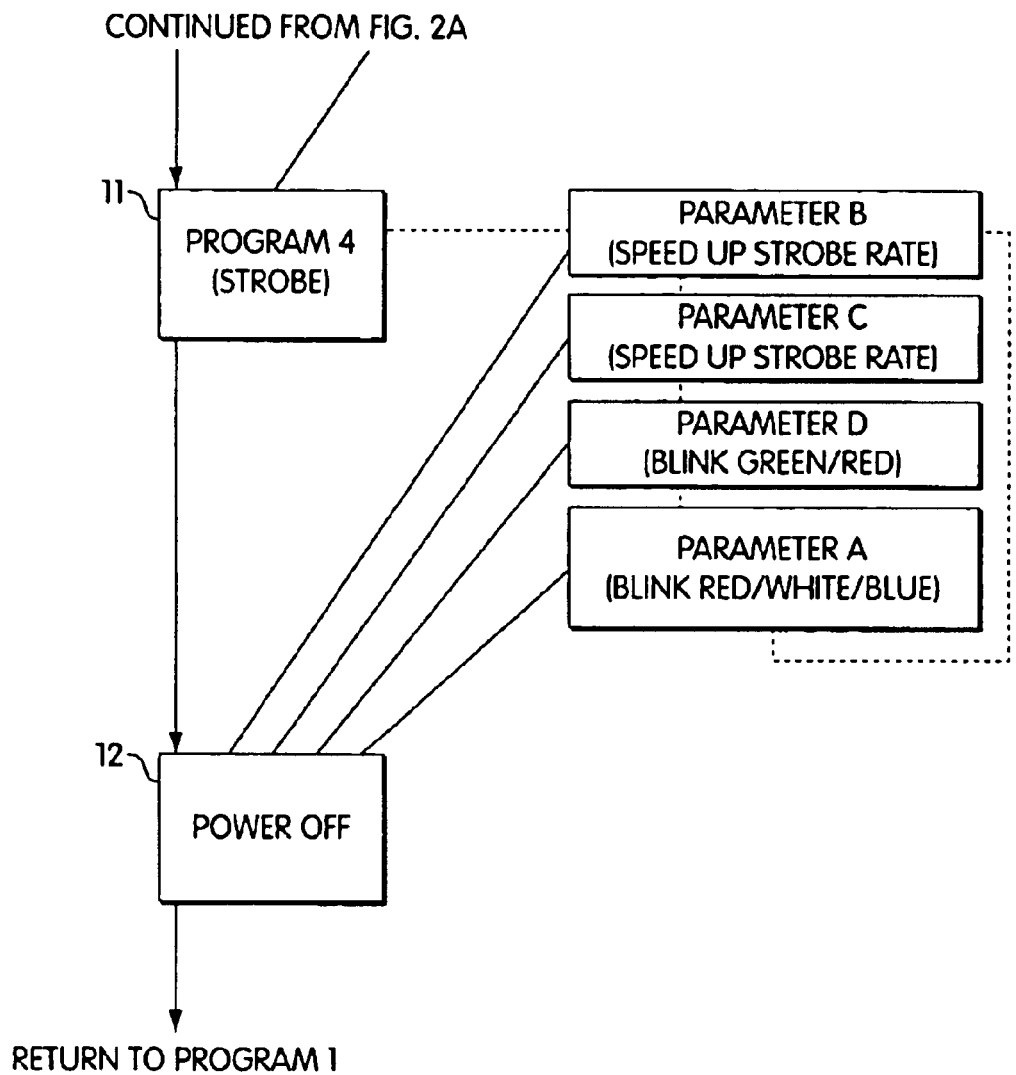

FIGS. 2A–2B are a state diagram of operation of a device according to the principles of the invention. The terms 'mode' and 'state' are used in the following description interchangeably. When the device is powered on, it may enter a first mode 8, for example, under control of a program executing on the processor 2 of FIG. 1. The first mode 8 may provide a color wash, in which the LEDs cycle continuously through the full color spectrum, or through some portion of the color spectrum. In the first mode 8, a rate of the color wash may be determined by a parameter stored, for example, in the memory 6 shown in FIG. 1A. Through a user interface such as a button, dial, slider, or the like, a user may adjust the rate of the color wash. Within each mode, the parameter may correspond to a different aspect of the lighting effect created by the mode, or each mode may access a different parameter so that persistence is maintained for a parameter during subsequent returns to that mode.

A second mode 9 may be accessed from the first mode 8. In the second mode 9, the device may randomly select a sequence of colors, and transition from one color to the next. The transitions may be faded to appear as continuous transitions, or they may be abrupt, changing in a single step from one random color to the next. The parameter may correspond to a rate at which these changes occur.

A third mode 10 may be accessed from the second mode 9. In the third mode, the device may provide a static, i.e., non-changing, color. The parameter may correspond to the frequency or spectral content of the color.

A fourth mode 11 may be accessed from the third mode 10. In the fourth mode 11, the device may strobe, that is, flash on and off. The parameter may correspond to the color of the strobe or the rate of the strobe. At a certain value, the parameter may correspond to other lighting effects, such as a strobe that alternates red, white, and blue, or a strobe that alternates green and red. Other modes, or parameters within a mode, may correspond to color changing effects coordinated with a specific time of the year or an event such as Valentine's Day, St. Patrick's Day, Easter, the Fourth of July, Halloween, Thanksgiving, Christmas, New Years or any other time, event, brand, logo, or symbol.

A fifth mode 12 may be accessed from the fourth mode 11. The fifth mode 12 may correspond to a power-off state. In the fifth mode 12, no parameter may be provided. A next transition may be to the first mode 8, or to some other mode. It will be appreciated that other lighting effects are known, and may be realized as modes or states that may be used with a device according to the principles of the invention.

A number of user interfaces may be provided for use with the device. Where, for example, a two-button interface is provided, a first button may be used to transition from mode to mode, while a second button may be used to control selection of a parameter within a mode. In this configuration, the second button may be held in a closed position, with a parameter changing incrementally until the button is released. The second button may be held, and a time that the button is held (until released) may be captured by the device, with this time being used to change the parameter. Or the parameter may change once each time that the second button is held and released. Some combination of these techniques may be used for different modes. For example, it will be appreciated that a mode having a large number of parameter values, such as a million or more different colors available through color changing LEDs, individually selecting each parameter value may be unduly cumbersome, and an approach permitting a user to quickly cycle through parameter values by holding the button may be preferred. By contrast, a mode with a small number of parameter values, such as five different strobe effects, may be readily controlled by stepping from parameter value to parameter value each time the second button is depressed.

A single button interface may instead be provided, where, for example, a transition between mode selections and parameter selections are signaled by holding the button depressed for a predetermined time, such as one or two seconds. That is, when the single button is depressed, the device may transition from one mode to another mode, with a parameter initialized at some predetermined value. If the button is held after it is depressed for the transition, the parameter value may increment (or decrement) so that the parameter may be selected within the mode. When the button is released, the parameter value may be maintained at its last value.

The interface may include a button and an adjustable input. The button may control transitions from mode to mode. The adjustable input may permit adjustment of a parameter value within the mode. The adjustable input may be, for example, a dial, a slider, a knob, or any other device whose physical position may be converted to a parameter value for use by the device. Optionally, the adjustable input may only respond to user input if the button is held after a transition between modes.

The interface may include two adjustable inputs. A first adjustable input may be used to select a mode, and a second adjustable input may be used to select a parameter within a mode. In another configuration, a single dial may be used to cycle through all modes and parameters in a continuous fashion. It will be appreciated that other controls are possible, including keypads, touch pads, sliders, switches, dials, linear switches, rotary switches, variable switches, thumb wheels, dual inline package switches, or other input devices suitable for human operation.

In one embodiment, a mode may have a plurality of associated parameters, each parameter having a parameter value. For example, in a color-changing strobe effect, a first parameter may correspond to a strobe rate, and a second parameter may correspond to a rate of color change. A device having multiple parameters for one or more modes may have a number of corresponding controls in the user interface.

The user interface may include user input devices, such as the buttons and adjustable controls noted above, that produce a signal or voltage to be read by the processor. They voltage may be a digital signal corresponding to a high and a low digital state. If the voltage is in the form of an analog voltage, an analog to digital converter (A/D) may be used to convert the voltage into a processor-useable digital form. The output from the A/D would then supply the processor with a digital signal. This may be useful for supplying signals to the lighting device through sensors, transducers, networks or from other signal generators.

The device may track time on an hourly, daily, weekly, monthly, or annual basis. Using an internal clock for this purpose, lighting effects may be realized on a timely basis for various Holidays or other events. For example, on Halloween the light may display lighting themes and color shows including, for example, flickering or washing oranges. On the Fourth of July, a red, white, and blue display may be provided. On December 25, green and red lighting may be displayed. Other themes may be provided for New Years, Valentine's Day, birthdays, etc. As another example, the device may provide different lighting effects at different times of day, or for different days of the week.

Figure 3:
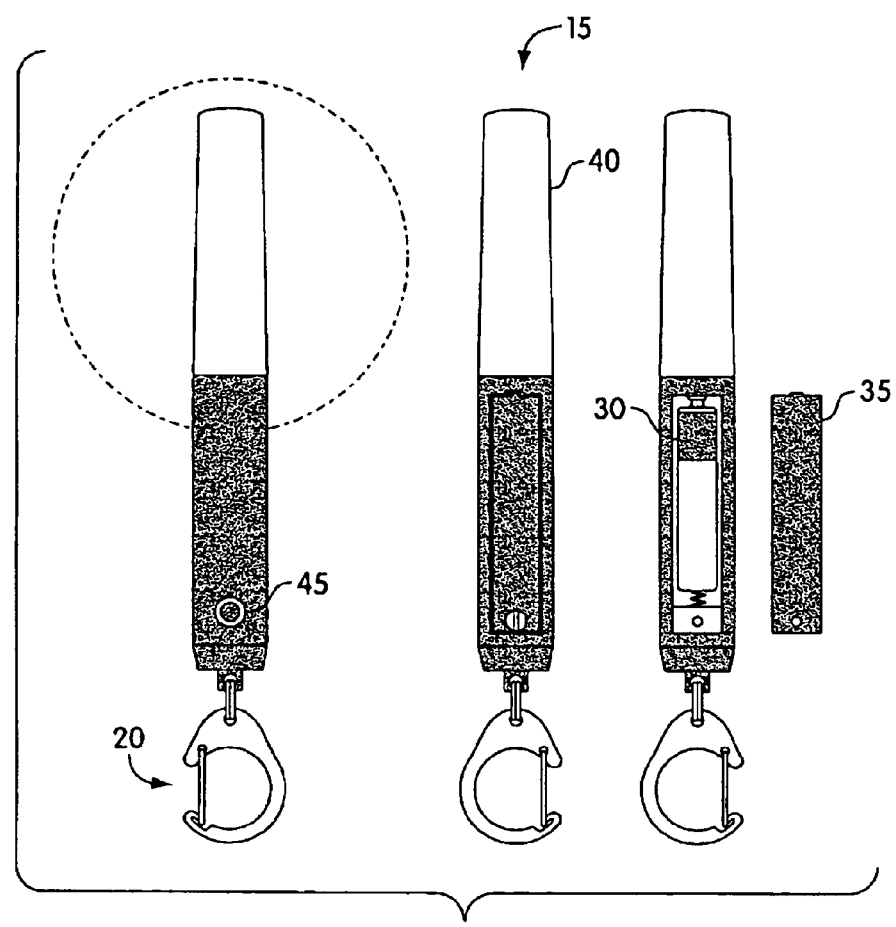
FIG. 3 shows a glow stick according to the principles of the invention.

FIG. 3 shows a glow stick according to the principles of the invention. The glow stick 15 may include the components described above with reference to FIG. 1, and may operate according to the techniques described above with reference to FIGS. 2A–2B. The glow stick 15 may be any small, cylindrical device that may hang from a lanyard, string, chain, bracelet, anklet, key chain, or necklace, for example, by a clip 20. The glow stick 15, as with many of the lighting devices described herein, may also be used as a handheld device. The glow stick 15 may operate from a battery 30 within the glow stick 10, such as an A, AA, AAA sized battery, or other battery. The battery 30 may be covered by a detachable portion 35 which hides the battery from view during normal use. An illumination lens 40 may encase a plurality of LEDs and diffuse color emanating therefrom. The lens 40 may be a light-transmissive material, such as a transparent material, translucent material, semi-transparent material, or other material suitable for this application. In general, the light-transmissive material may be any material that receives light emitted from one or more LEDs and displays one or more colors that are a combination of the spectra of the plurality of LEDs. A user interface 45 may be included for providing user input to control operation of the glow stick 15. In the embodiment depicted in FIG. 2, the user interface 45 is a single button, however it will be appreciated that any of the interfaces discussed above may suitably be adapted to the glow stick 10. The user interface 45 may be a switch, button or other device that generates a signal to a processor that controls operation of the glow stick 15.

Figure 4:
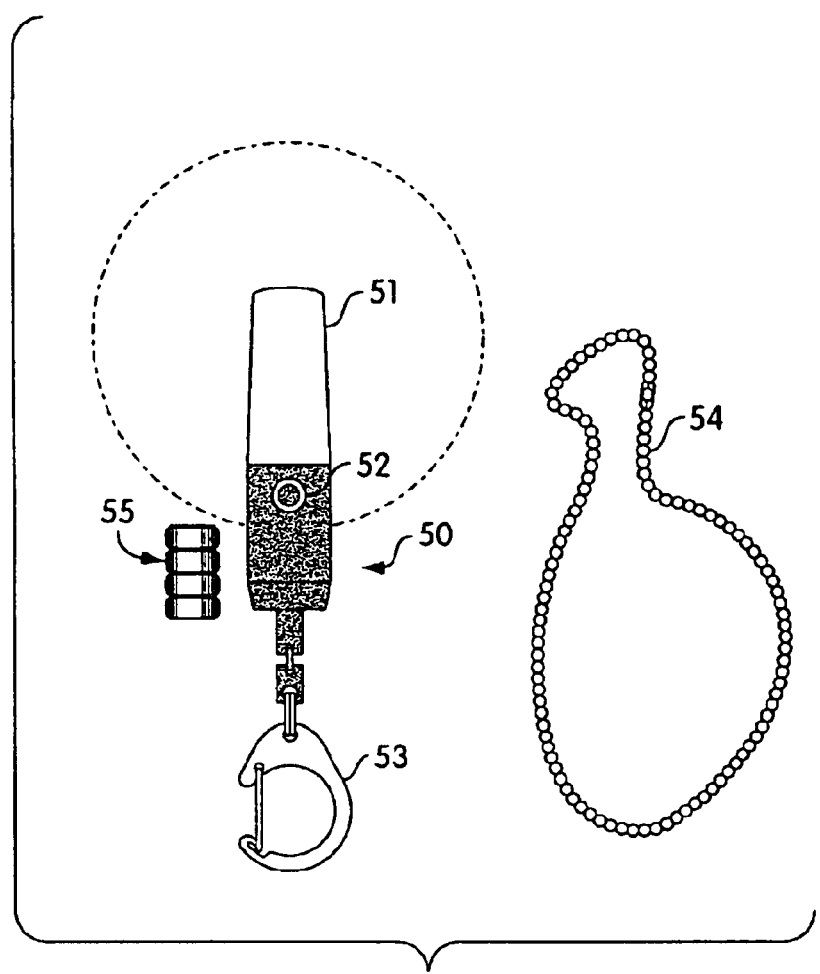
FIG. 4 shows a key chain according to the principles of the invention.

FIG. 4 shows a key chain according to the principles of the invention. The key chain 50 may include a light-transmissive material 51 enclosing one or more LEDs and a system such as the system of FIG. 1 (not shown), a one-button user interface 52, a clip 53 suitable for connecting to a chain 54, and one or more batteries 55. The key chain 50 may be similar to the glow stick 15 of FIG. 2, although it may be of smaller size. To accommodate the smaller size, more compact batteries 55 may be used. The key chain 50 may operate according to the techniques described above with reference to FIGS. 2A–2B.

Figure 5:
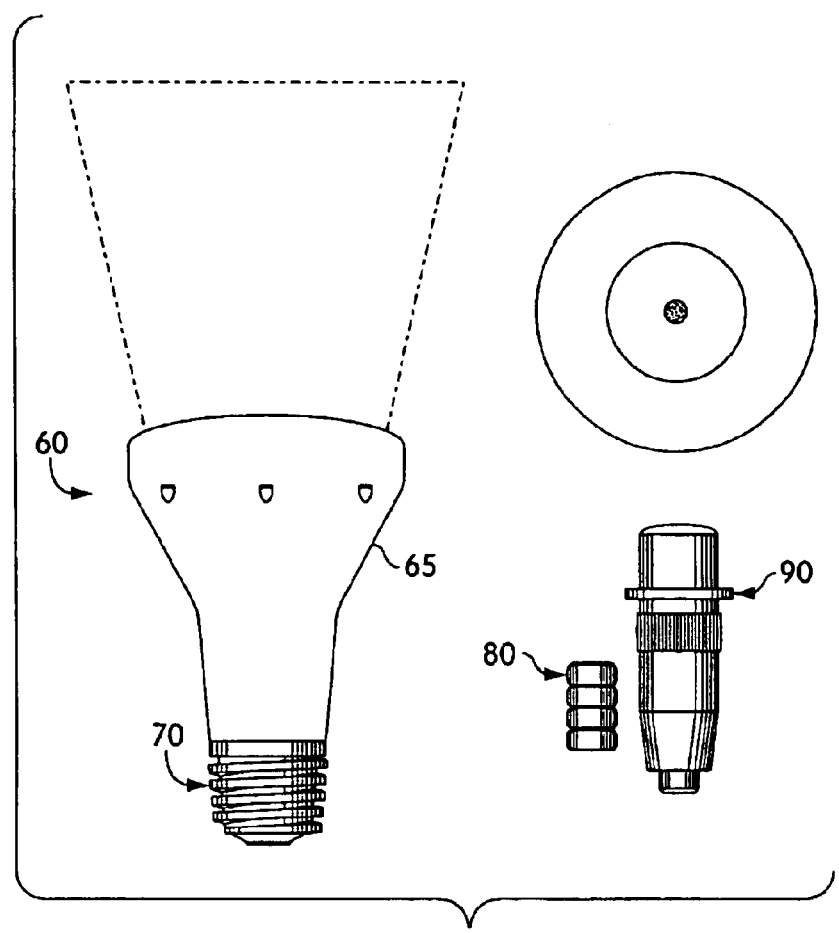
FIG. 5 shows a spotlight according to the principles of the invention.

FIG. 5 shows a spotlight according to the principles of the invention. The spotlight 60 may include a system such as that depicted in FIG. 1 for controlling a plurality of LEDs within the spotlight 60, and may operate according to the techniques described above with reference to FIGS. 2A–2B. The spotlight 60 may include a housing 65 suitable for use with convention lighting fixtures, such as those used with AC spotlights, and including a light-transmissive material on one end to permit LEDs to illuminate through the housing 65. The spotlight configurations may be provided to illuminate an object or for general illumination for example and the material may not be required. The mixing of the colors may take place in the projection of the beam for example. The spotlight 60 may draw power for illumination from an external power source through a connection 70, such as an Edison mount fixture, plug, bi-pin base, screw base, base, Edison base, spade plug, and power outlet plug or any other adapter for adapting the spotlight 60 to external power. The connection 70 may include a converter to convert received power to power that is useful for the spotlight. For example, the converter may include an AC to DC converter to convert one-hundred twenty Volts at sixty Hertz into a direct current at a voltage of, for example, five Volts or twelve Volts. The spotlight 60 may also be powered by one or more batteries 80, or a processor in the spotlight 60 may be powered by one or more batteries 80, with LEDs powered by electrical power received through the connection 70. A battery case 90 may be integrated into the spotlight 60 to contain the one or more batteries 80.

The connector 70 may include any one of a variety of adapters to adapt the spotlight 60 to a power source. The connector 70 may be adapted for, for example, a screw socket, socket, post socket, pin socket, spade socket, wall socket, or other interface. This may be useful for connecting the lighting device to AC power or DC power in existing or new installations. For example, a user may want to deploy the spotlight 60 in an existing one-hundred and ten VAC socket. By incorporating an interface to this style of socket into the spotlight 60, the user can easily screw the new lighting device into the socket. U.S. patent application Ser. No. 09/213,537, entitled "Power/Data Protocol" describes techniques for transmitting data and power along the same lines and then extracting the data for use in a lighting device. The methods and systems disclosed therein could also be used to communicate information to the spotlight 60 of FIG. 4, through the connector 70.

Figure 6:
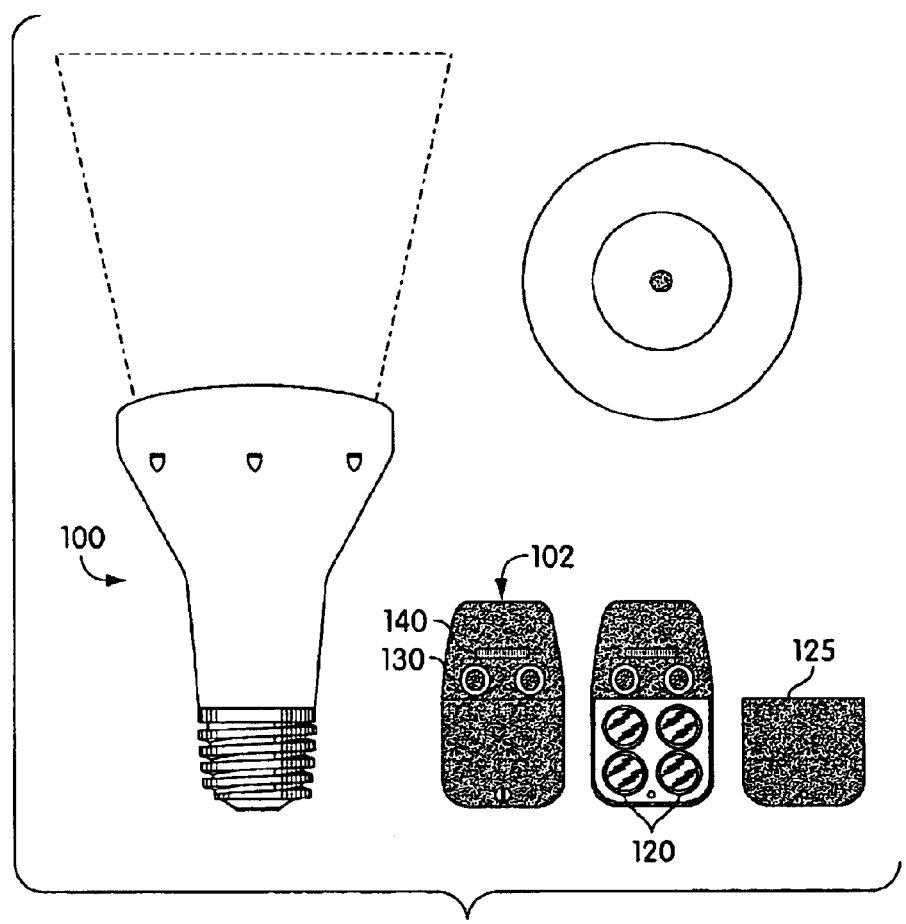
FIG. 6 shows a spotlight according to the principles of the invention.

FIG. 6 shows a spotlight according to the principles of the invention. The spotlight 100 may be similar to the spotlight of FIG. 4. A remote user interface 102 may be provided, powered by one or more batteries 120 that are covered by a removable battery cover 125. The remote user interface 102 may include, for example, one or more buttons 130 and a dial 140 for selecting modes and parameters. The remote user interface 102 may be remote from the spotlight 100, and may transmit control information to the spotlight 100 using, for example, an infrared or radio frequency communication link, with corresponding transceivers in the spotlight 100 and the remote user interface 102. The information could be transmitted through infrared, RF, microwave, electromagnetic, or acoustic signals, or any other transmission medium. The transmission could also be carried, for its complete path or a portion thereof, through a wire, cable, fiber optic, network or other transmission medium.

Figure 7:
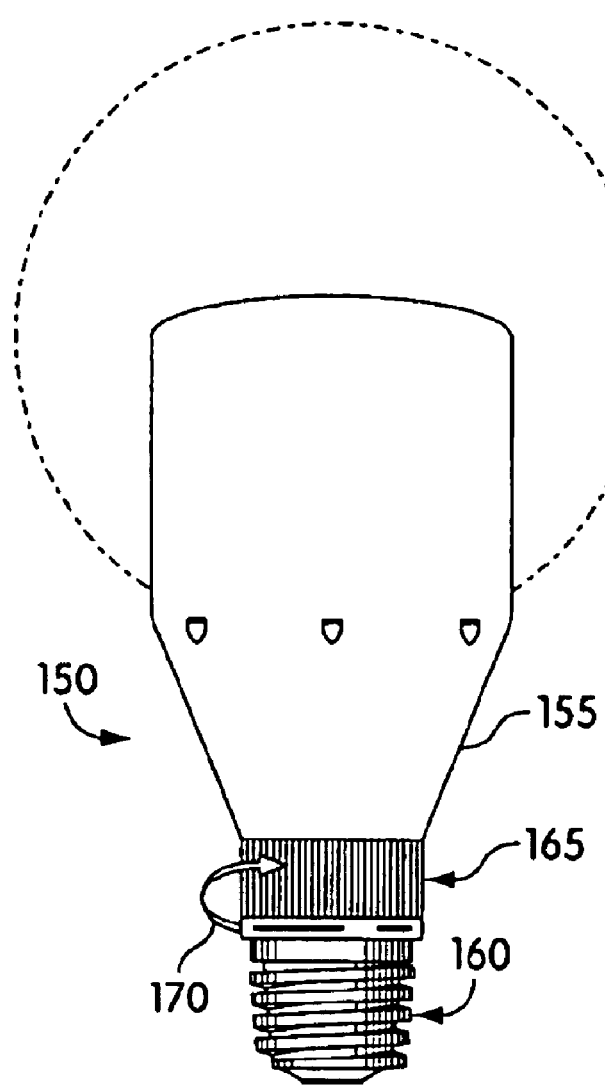
FIG. 7 shows an Edison mount light bulb according to the principles of the invention.

FIG. 7 shows an Edison mount light bulb according to the principles of the invention. The light bulb 150 may include a system such as that depicted in FIG. 1 for controlling a plurality of LEDs within the light bulb 150, and may operate according to the techniques described above with reference to FIGS. 1B–1C. The light bulb 150 may include a housing 155 suitable for use with convention lighting fixtures, such as those used with AC light bulbs, and including a light-transmissive material on one end to permit LEDs to illuminate through the housing 155. In the embodiment of FIG. 6, the light bulb 150 includes a screw base 160, and a user interface 165 in the form of a dial integrated into the body of the light bulb 150. The dial may be rotated, as indicated by an arrow 170, to select modes and parameters for operation of the light bulb 150.

Figure 8:
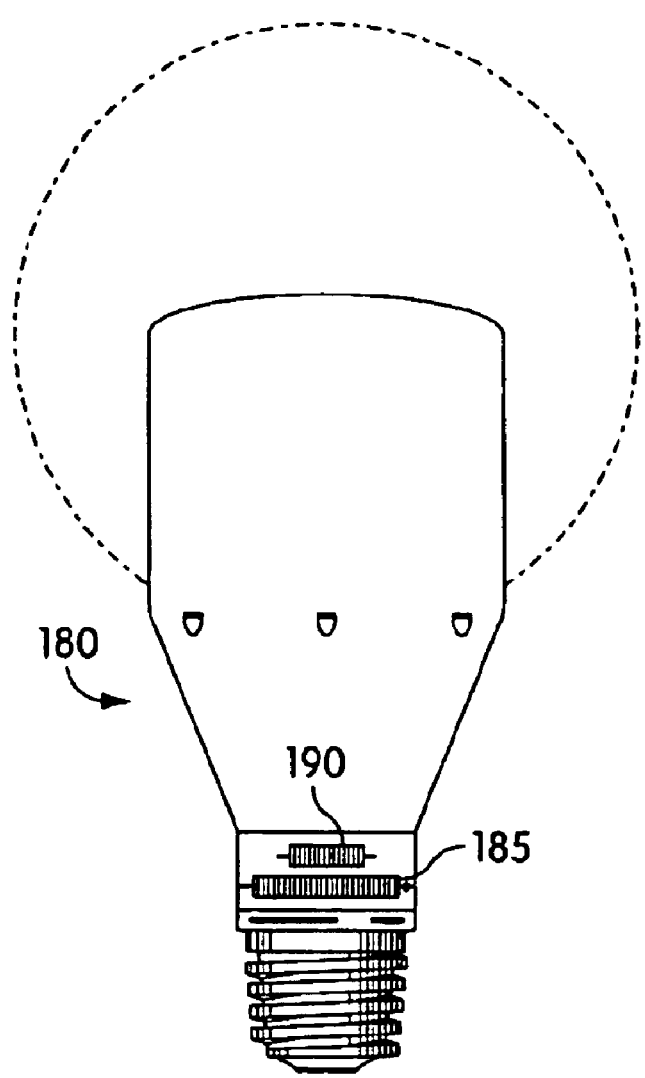
FIG. 8 shows an Edison mount light bulb according to the principles of the invention.

FIG. 8 shows an Edison mount light bulb according to the principles of the invention. The light bulb 180 is similar to the light bulb 150 of FIG. 6, with a different user interface. The user interface of the light bulb 180 includes a thumbwheel 185 and a two-way switch 190. In this embodiment, the switch 190 may be used to move forward and backward through a sequence of available modes. For example, if the light bulb 180 has four modes numbered 1–4, by sliding the switch 190 to the left in FIG. 7, the mode may move up one mode, i.e., from mode 1 to mode 2. By sliding the switch 190 to the right in FIG. 7, the mode may move down one mode, i.e., from mode 2 to mode 1. The switch 190 may include one or more springs to return the switch 190 to a neutral position when force is not applied. The thumbwheel 185 may be constructed for endless rotation in a single direction, in which case a parameter controlled by the thumbwheel 185 may reset to a minimum value after reaching a maximum value (or vice versa). The thumbwheel may be constructed to have a predefined span, such as one and one-half rotations. In this latter case, one extreme of the span may represent a minimum parameter value and the other extreme of the span may represent a maximum parameter value. In an embodiment, the switch 190 may control a mode (left) and a parameter (right), and the thumbwheel 185 may control a brightness of the light bulb 180.

A light bulb such as the light bulb 180 of FIG. 7 may also be adapted to control through conventional lighting control systems. Many incandescent lighting systems have dimming control that is realized through changes in applied voltages, typically either through changes to applied voltages or chopping an AC waveform. A power converter can be used within the light bulb 180 to convert the received power, whether in the form of a variable amplitude AC signal or a chopped waveform, to the requisite power for the control circuitry and the LEDs, and where appropriate, to maintain a constant DC power supply for digital components. An analog-to-digital converter may be included to digitize the AC waveform and generate suitable control signals for the LEDs. The light bulb 180 may also detect and analyze a power supply signal and make suitable adjustments to LED outputs. For example, a light bulb 180 may be programmed to provide consistent illumination whether connected to a one-hundred and ten VAC, 60 Hz power supply or a two-hundred and twenty VAC, 50 Hz power supply.

Control of the LEDs may be realized through a look-up table that correlates received AC signals to suitable LED outputs for example. The look-up table may contain full brightness control signals and these control signals may be communicated to the LEDs when a power dimmer is at 100%. A portion of the table may contain 80% brightness control signals and may be used when the input voltage to the lamp is reduced to 80% of the maximum value. The processor may continuously change a parameter with a program as the input voltage changes. The lighting instructions could be used to dim the illumination from the lighting system as well as to generate colors, patterns of light, illumination effects, or any other instructions for the LEDs. This technique could be used for intelligent dimming of the lighting device, creating color-changing effects using conventional power dimming controls and wiring as an interface, or to create other lighting effects. In an embodiment both color changes and dimming may occur simultaneously. This may be useful in simulating an incandescent dimming system where the color temperature of the incandescent light becomes warmer as the power is reduced.

Three-way light bulbs are also a common device for changing illumination levels. These systems use two contacts on the base of the light bulb and the light bulb is installed into a special electrical socket with two contacts. By turning a switch on the socket, either contact on the base may be connected with a voltage or both may be connected to the voltage. The lamp includes two filaments of different resistance to provide three levels of illumination. A light bulb such as the light bulb 180 of FIG. 7 may be adapted to use with a three-way light bulb socket. The light bulb 180 could have two contacts on the base and a look-up table, a program, or other system within the light bulb 180 could contain control signals that correlate to the socket setting. Again, this could be used for illumination control, color control or any other desired control for the LEDs.

This system could be used to create various lighting effects in areas where standard lighting devices where previously used. The user can replace existing incandescent light bulbs with an LED lighting device as described herein, and a dimmer on a wall could be used to control color-changing effects within a room. Color changing effects may include dimming, any of the color-changing effects described above, or any other color-changing or static, colored effects.

Figure 9:
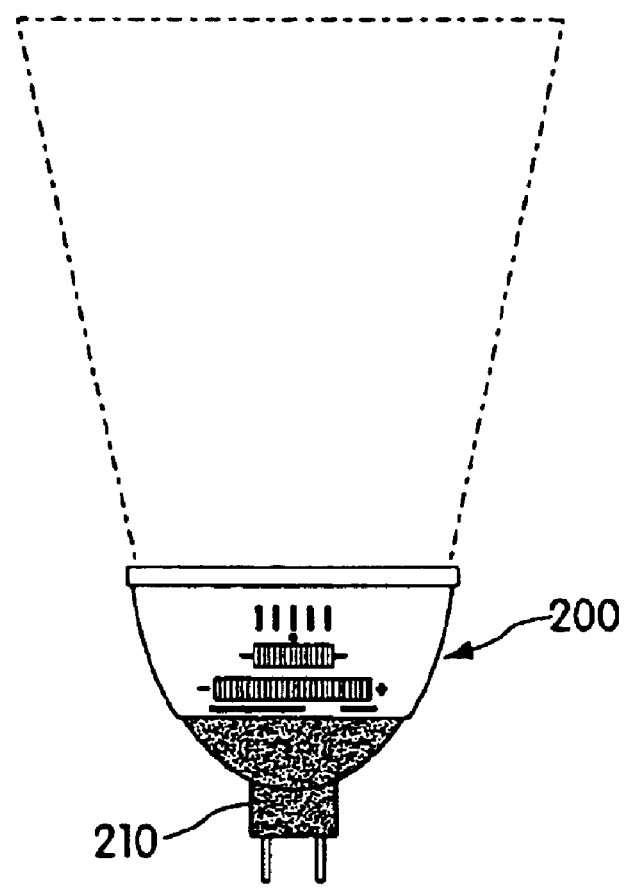
FIG. 9 shows a light bulb according to the principles of the invention.

FIG. 9 shows a light bulb according to the principles of the invention. As seen in FIG. 8, the light bulb 200 may operate from fixtures other than Edison mount fixtures, such as an MR-16, low voltage fixture 210 that may be used with direct current power systems.

Figure 10:
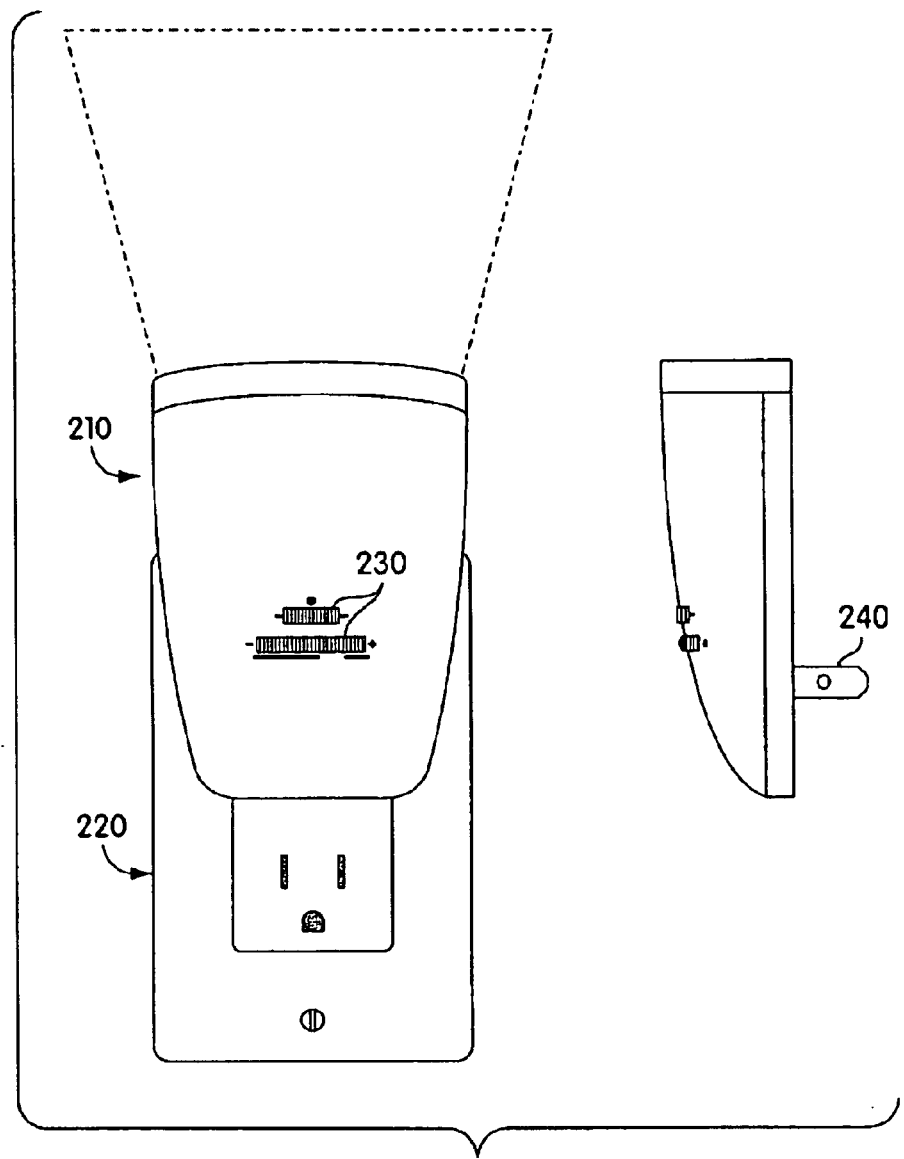
FIG. 10 shows a wall socket mounted light according to the principles of the invention.

FIG. 10 shows a wall socket mounted light according to the principles of the invention. The light 210 may include a plug adapted to, for example, a one-hundred and ten volt alternating current outlet 220 constructing according to ANSI specifications. The light 210 may include a switch and thumbwheel as a user interface 230, and one or more spades 240 adapted for insertion into the outlet 220. The body of the light 210 may include a reflective surface for directing light onto a wall for color changing wall washing effects.

Figure 11:
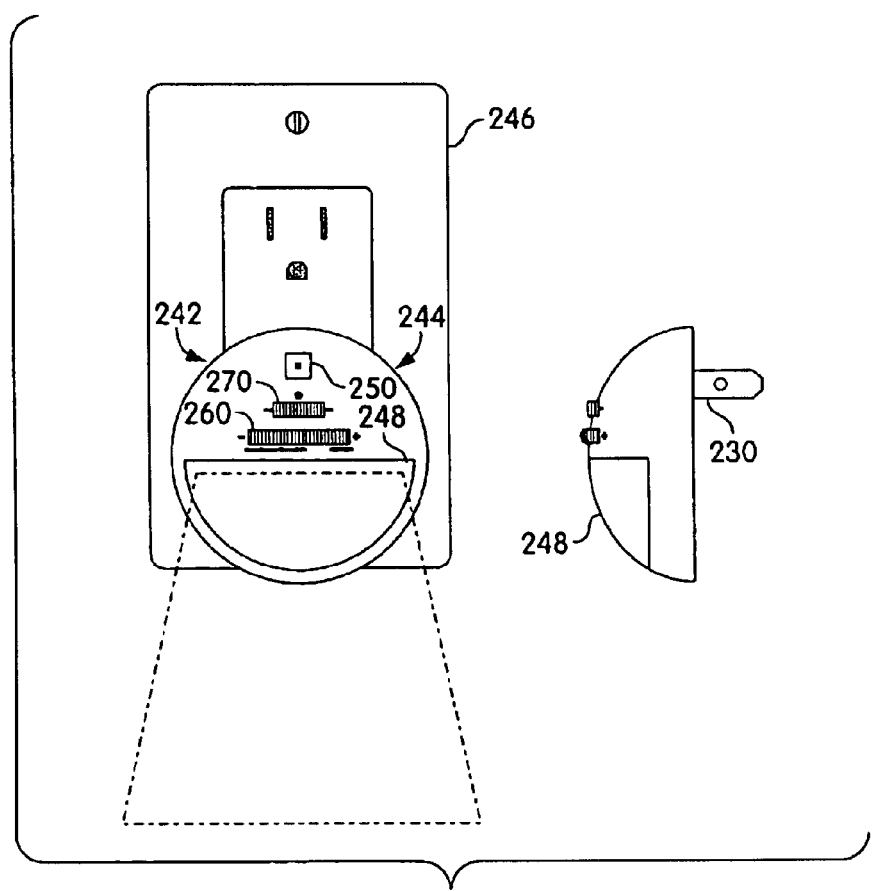
FIG. 11 shows a night light according to the principles of the invention.

FIG. 11 shows a night light according to the principles of the invention. The night light 242 may include a plug 244 adapted to, for example, a one-hundred and ten volt alternating current outlet 246. The night light 242 may include a system such as that depicted in FIG. 1 for controlling a plurality of LEDs within the night light 242, and may operate according to the techniques described above with reference to FIGS. 1B–1C. The night light 242 may include a light-transmissive material 248 for directing light from the LEDs, e.g., in a downward direction. The night light 242 may also include a sensor 250 for detecting low ambient lighting, such that the night light 242 may be activated only when low lighting conditions exist. The sensor 250 may generate a signal to the processor to control activation and display type of the night light 242. The night light 242 may also include a clock/calendar, such as that the seasonal lighting displays described above may be realized. The night light 242 may include a thumbwheel 260 and a switch 270, such as those described above, for selecting a mode and a parameter. As with several of the above embodiments, the night light 242 may include a converter that generates DC power suitable to the control circuitry of the night light 242.

Figure 12:
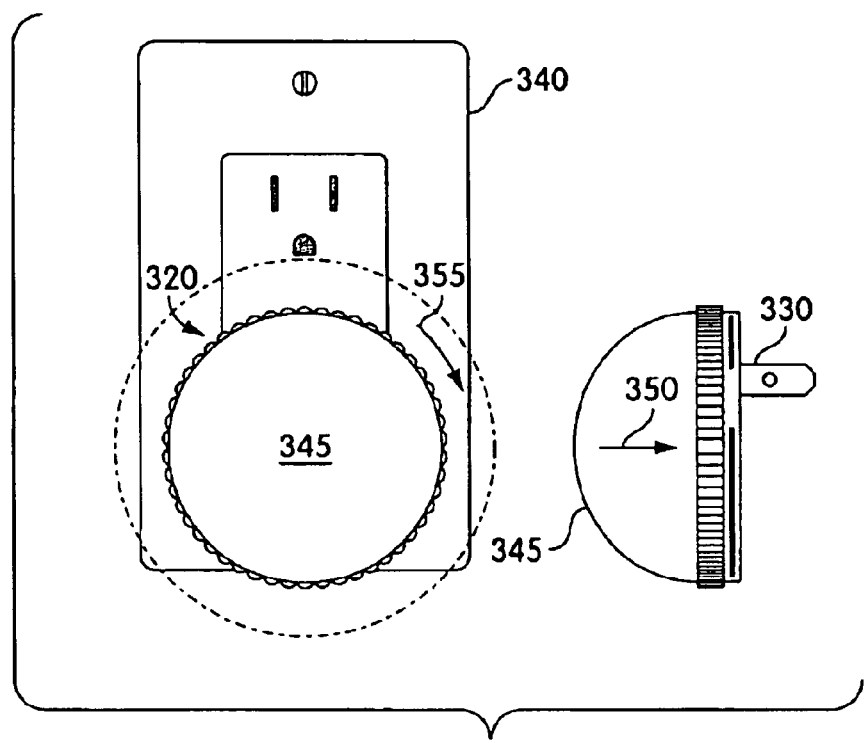
FIG. 12 shows a night light according to the principles of the invention.

FIG. 12 shows a night light according to the principles of the invention. The night light 320 may include a plug 330 adapted to, for example, a one-hundred and ten volt alternating current outlet 340. The night light 320 may include a system such as that depicted in FIG. 1 for controlling a plurality of LEDs within the night light 320, and may operate according to the techniques described above with reference to FIGS. 1B–1C. The night light 320 may include a light-transmissive dome 345. The night light 320 may also include a sensor within the dome 345 for detecting low ambient lighting, such that the night light 320 may be automatically activated when low lighting conditions exist. The night light 320 may also include a clock/calendar, such as that the seasonal lighting displays described above may be realized. In the embodiment of FIG. 11, the dome 345 of the night light 320 may also operate as a user interface. By depressing the dome 345 in the direction of a first arrow 350, a mode may be selected. By rotating the dome 345 in the direction of a second arrow 355, a parameter may be selected within the mode. As with several of the above embodiments, the night light 220 may include a converter that generates DC power suitable to the control circuitry of the night light 220.

As will be appreciated from the foregoing examples, an LED system such as that described in reference to FIGS. 1 & 2A–2B may be adapted to a variety of lighting applications, either as a replacement for conventional light bulbs, including incandescent light bulbs, halogen light bulbs, tungsten light bulbs, fluorescent light bulbs, and so forth, or as an integrated lighting fixture such as a desk lamp, vase, night light, lantern, paper lantern, designer night light, strip light, cove light, MR light, wall light, screw based light, lava lamp, orb, desk lamp, decorative lamp, string light, or camp light. The system may have applications to architectural lighting, including kitchen lighting, bathroom lighting, bedroom lighting, entertainment center lighting, pool and spa lighting, outdoor walkway lighting, patio lighting, building lighting, facade lighting, fish tank lighting, or lighting in other areas where light may be employed for aesthetic effect. The system could be used outdoors in sprinklers, lawn markers, pool floats, stair markers, in-ground markers, or door bells, or more generally for general lighting, ornamental lighting, and accent lighting in indoor or outdoor venues. The systems may also be deployed where functional lighting is desired, as in brake lights, dashboard lights, or other automotive and vehicle applications.

Color-changing lighting effects may be coordinated among a plurality of the lighting devices described herein. Coordinated effects may be achieved through conventional lighting control mechanisms where, for example, each one of a plurality of lighting devices is programmed to respond differently, or with different start times, to a power-on signal or dimmer control signal delivered through a conventional home or industrial lighting installation.

Each lighting device may instead be addressed individually through a wired or wireless network to control operation thereof. The LED lighting devices may have transceivers for communicating with a remote control device, or for communicating over a wired or wireless network.

It will be appreciated that a particular lighting application may entail a particular choice of LED. Pre-packaged LEDs generally come in a surface mount package or a T package. The surface mount LEDs have a very large beam angle, the angle at which the light intensity drops to 50% of the maximum light intensity, and T packages may be available in several beam angles. Narrow beam angles project further with relatively little color mixing between adjacent LEDs. This aspect of certain LEDs may be employed for projecting different colors simultaneously, or for producing other effects. Wider angles can be achieved in many ways such as, but not limited to, using wide beam angle T packages, using surface mount LEDs, using un-packaged LEDs, using chip on board technology, or mounting the die on directly on a substrate as described in U.S. Prov. Patent App. No. 60/235, 966, entitled "Optical Systems for Light Emitting Semiconductors." A reflector may also be associated with one or more LEDs to project illumination in a predetermined pattern. One advantage of using the wide-beam-angle light source is that the light can be gathered and projected onto a wall while allowing the beam to spread along the wall. This accomplishes the desired effect of concentrating illumination on the wall while colors projected from separate LEDs mix to provide a uniform color.

Figure 13:
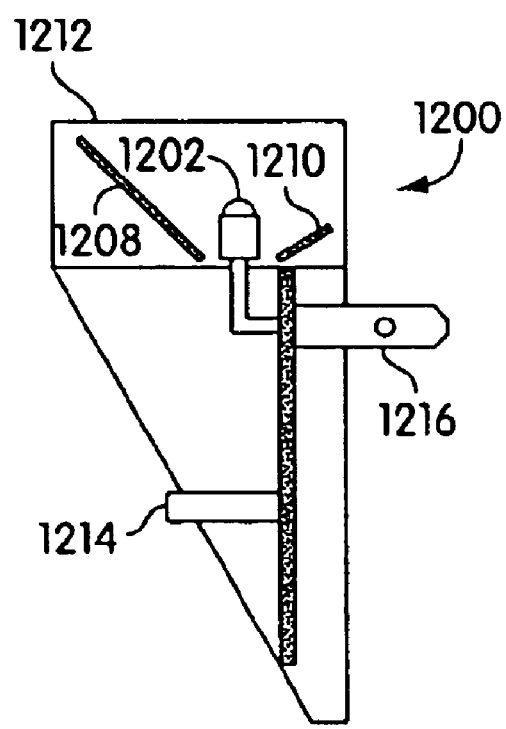
FIG. 13 shows a wall washing light according to the principles of the invention.

FIG. 13 illustrates a lighting device 1200 with at least one LED 1202. There may be a plurality of LEDs 1202 of different colors, or a plurality of LEDs 1202 of a single color, such as to increase intensity or beam width of illumination for that color, or a combination of both. A reflector including a front section 1208 and a rear section 1210 may also be included in the device 1200 to project light from the LED. This reflector can be formed as several pieces or one piece of reflective material. The reflector may direct illumination from the at least one LED 1202 in a predetermined direction, or through a predetermined beam angle. The reflector may also gather and project illumination scattered by the at least one LED 1202. As with other examples, the lighting device 1200 may include a light-transmissive material 1212, a user interface 1214, and a plug 1216.

Figure 14:
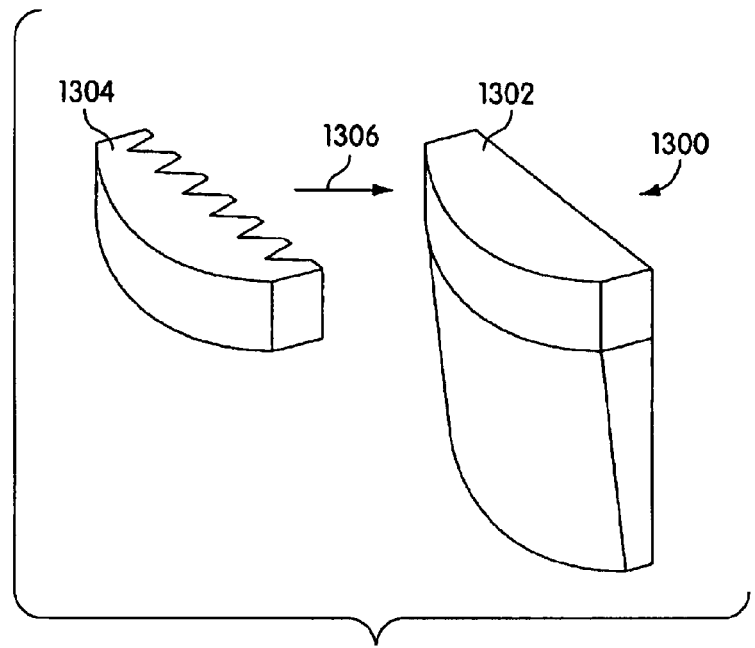
FIG. 14 shows a wall washing light according to the principles of the invention.

FIG. 14 shows another embodiment of a wall washing light according to the principles of the invention. The night light 1300 may include an optic 1302 formed from a light-transmissive material and a detachable optic 1304. The detachable optic 1304 may fit over the optic 1302 in a removable and replaceable fashion, as indicated by an arrow 1306, to provide a lighting effect, which may include filtering, diffusing, focusing, and so forth. The detachable optic 1304 may direct illumination from the night light 1300 into a predetermined shape or image, or spread the spectrum of the illumination in a prismatic fashion. The detachable optic 1304 may, for example, have a pattern etched into including, for example, a saw tooth, slit, prism, grating, squares, triangles, half-tone screens, circles, semi-circles, stars or any other geometric pattern. The pattern can also be in the form of object patterns such as, but not limited to, trees, stars, moons, suns, clovers or any other object pattern. The detachable optic 1304 may also be a holographic lens. The detachable optic 1304 may also be an anamorphic lens configured to distort or reform an image. These patterns can also be formed such that the projected light forms a non-distorted pattern on a wall, provided the geometric relationship between the wall and the optic is known in advance. The pattern could be designed to compensate for the wall projection. Techniques for applying anamorphic lenses are described, for example, in "Anamorphic Art and Photography—Deliberate Distortions That Can Be Easily Undone," *Optics and Photonics News*, November 1992, the teachings of which are incorporated herein by reference. The detachable optic 1304 may include a multi-layered lens. At least one of the lenses in a multi-layered lens could also be adjustable to provide the user with adjustable illumination patterns.

Figure 15:
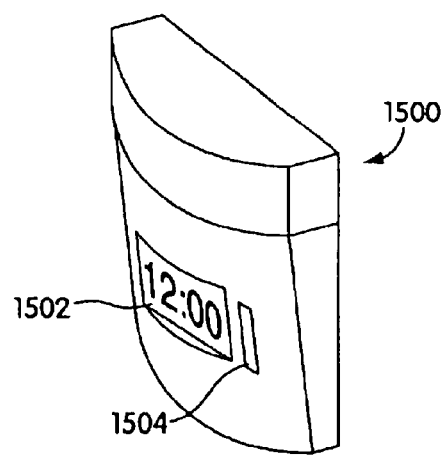
FIG. 15 shows a light according to the principles of the invention.

FIG. 15 shows a lighting device according to the principles of the invention. The lighting device 1500 may be any of the lighting devices described above. The lighting device may include a display screen 1502. The display screen 1502 can be any type of display screen such as, but not limited to, an LCD, plasma screen, backlit display, edgelit display, monochrome screen, color screen, screen, or any other type of display. The display screen 1502 could display information for the user such as the time of day, a mode or parameter value for the lighting device 1500, a name of a mode, a battery charge indication, or any other information useful to a user of the lighting device 1500. A name of a mode may be a generic name, such as 'strobe', 'static', and so forth, or a fanciful name, such as 'Harvard' for a crimson illumination or 'Michigan' for a blue-yellow fade or wash. Other names may be given to, and displayed for, modes relating to a time of the year, holidays, or a particular celebration. Other information may be displayed, including a time of the day, days left in the year, or any other information. The display information is not limited to characters; the display screen 1502 could show pictures or any other information. The display screen 1502 may operate under control of the processor 2 of FIG. 1. The lighting device 1500 may include a user interface 1504 to control, for example the display screen 1502, or to set a time or other information displayed by the display screen 1502, or to select a mode or parameter value.

The lighting device 1500 may also be associated with a network, and receive network signals. The network signals could direct the night-light to project various colors as well as depict information on the display screen 1502. For example, the device could receive signals from the World Wide Web and change the color or projection patterns based on the information received. The device may receive outside temperature data from the Web or other device and project a color based on the temperature. The colder the temperature the more saturated blue the illumination might become, and as the temperature rises the lighting device 1500 might project red illumination. The information is not limited to temperature information. The information could be any information that can be transmitted and received. Another example is financial information such as a stock price. When the stock price rises the projected illumination may turn green, and when the price drops the projected illumination may turn red. If the stock prices fall below a predetermined value, the lighting device 1500 may strobe red light or make other indicative effects.

It will be appreciated that systems such as those described above, which receive and interpret data, and generate responsive color-changing illumination effects, may have broad application in areas such as consumer electronics. For example, information be obtained, interpreted, and converted to informative lighting effects in devices such as a clock radio, a telephone, a cordless telephone, a facsimile machine, a boom box, a music box, a stereo, a compact disk player, a digital versatile disk player, an MP3 player, a cassette player, a digital tape player, a car stereo, a television, a home audio system, a home theater system, a surround sound system, a speaker, a camera, a digital camera, a video recorder, a digital video recorder, a computer, a personal digital assistant, a pager, a cellular phone, a computer mouse, a computer peripheral, or an overhead projector.

Figure 16:
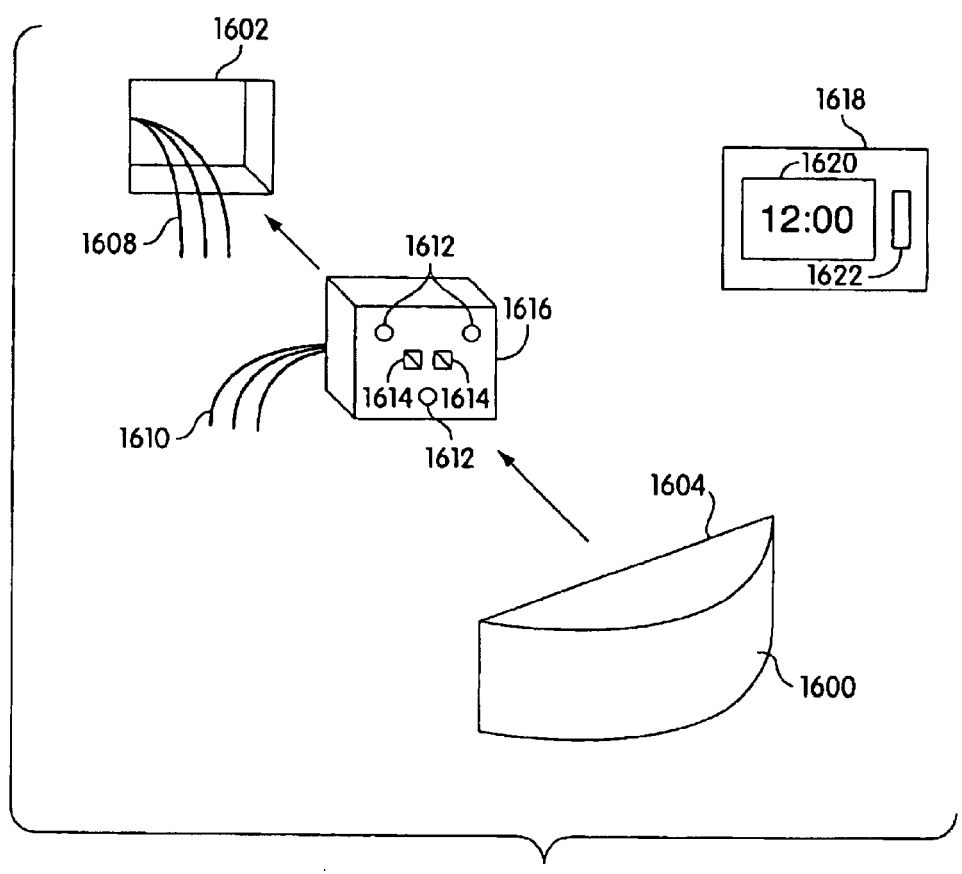
FIG. 16 shows a lighting system according to the principles of the invention.

FIG. 16 depicts a modular unit. A lighting device 1600 may contain one or more LEDs and a decorative portion of a lighting fixture. An interface box 1616 could contain a processor, memory, control circuitry, and a power supply to convert the AC to DC to operate the lighting device 1600. The interface box 1616 may have standard power wiring 1610 to be connected to a power connection 1608. The interface box 1616 can be designed to fit directly into a standard junction box 1602. The interface box 1616 could have physical connection devices 1612 to match connections on a backside 1604 of the lighting device 1600. The physical connection devices 1612 could be used to physically mount the lighting device 1600 onto the wall. The interface box 1616 could also include one or more electrical connections 1614 to bring power to the lighting device 1600. The electrical connections 1614 may include connections for carrying data to the interface box 1616, or otherwise communicating with the interface box 1616 or the lighting device 1600. The connections 1614 and 1612 could match connections on the backside 1604 of the lighting device 1600. This would make the assembly and changing of lighting devices 1600 easy. These systems could have the connectors 1612 and 1614 arranged in a standard format to allow for easy changing of lighting devices 1600. It will be obvious to one with ordinary skill in the art that the lighting fixture 1600 could also contain some or all of the circuitry.

The lighting devices 1600 could also contain transmitters and receivers for transmitting and receiving information. This could be used to coordinate or synchronize several lighting devices 1600. A control unit 1618 with a display screen 1620 and interface 1622 could also be provided to set the modes of, and the coordination between, several lighting devices 1600. This control unit 1618 could control the lighting device 1600 remotely. The control unit 1618 could be placed in a remote area of the room and communicate with one or more lighting devices 1600. The communication could be accomplished using any communication method such as, but not limited to, RF, IR, microwave, acoustic, electromagnetic, cable, wire, network or other communication method. Each lighting device 1600 could also have an addressable controller, so that each one of a plurality of lighting devices 1600 may be individually accessed by the control unit 1618, through any suitable wired or wireless network.

Figure 17:
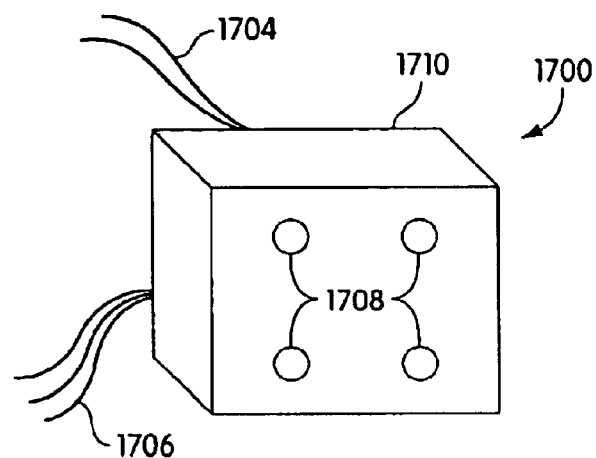
FIG. 17 shows a light according to the principles of the invention.

FIG. 17 shows a modular topology for a lighting device. In this modular configuration, a light engine 1700 may include a plurality of power connectors 1704 such as wires, a plurality of data connectors 1706, such as wires, and a plurality of LEDs 1708, as well as the other components described in reference to FIGS. 1 and 2A–2B, enclosed in a housing 1710. The light engine 1700 may be used in lighting fixtures or as a stand-alone device. The modular configuration may be amenable to use by lighting designers, architects, contractors, technicians, users or other people designing or installing lighting, who may provide predetermined data and power wiring throughout an installation, and locate a light engine 1700 at any convenient location therein.

Optics may be used to alter or enhance the performance of illumination devices. For example, reflectors may be used to redirect LED radiation, as described in U.S. Patent Application No. 60/235,966 "Optical Systems for Light Emitting Semiconductors," the teachings of which are incorporated herein by reference. U.S. Patent Application No. 60/235,966 is incorporated by reference herein.

Figure 18:
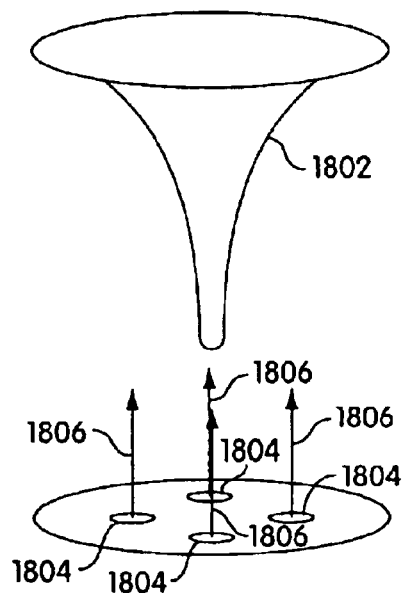
FIG. 18 shows a light and reflector arrangement according to the principles of the invention.

FIG. 18 shows a reflector that may be used with the systems described herein. As shown in FIG. 18, a contoured reflective surface 1802 may be placed apart from a plurality of LEDs 1804, such that radiation from the LEDs 1804 is directed toward the reflective surface 1802, as indicated by arrows 1806. In this configuration, radiation from the LEDs 1804 is redirected out in a circle about the reflective surface 1802. The reflective surface 1802 may have areas of imperfections or designs to create projection effects. The LEDs 1804 can be arranged to uniformly project the light onto the reflector or they can be arranged with a bias to increase the illumination on certain sections of the reflector. The individual LEDs 1804 of the plurality of LEDs 1804 can also be independently controlled. This technique can be used to create light patterns or color effects.

Figure 19:
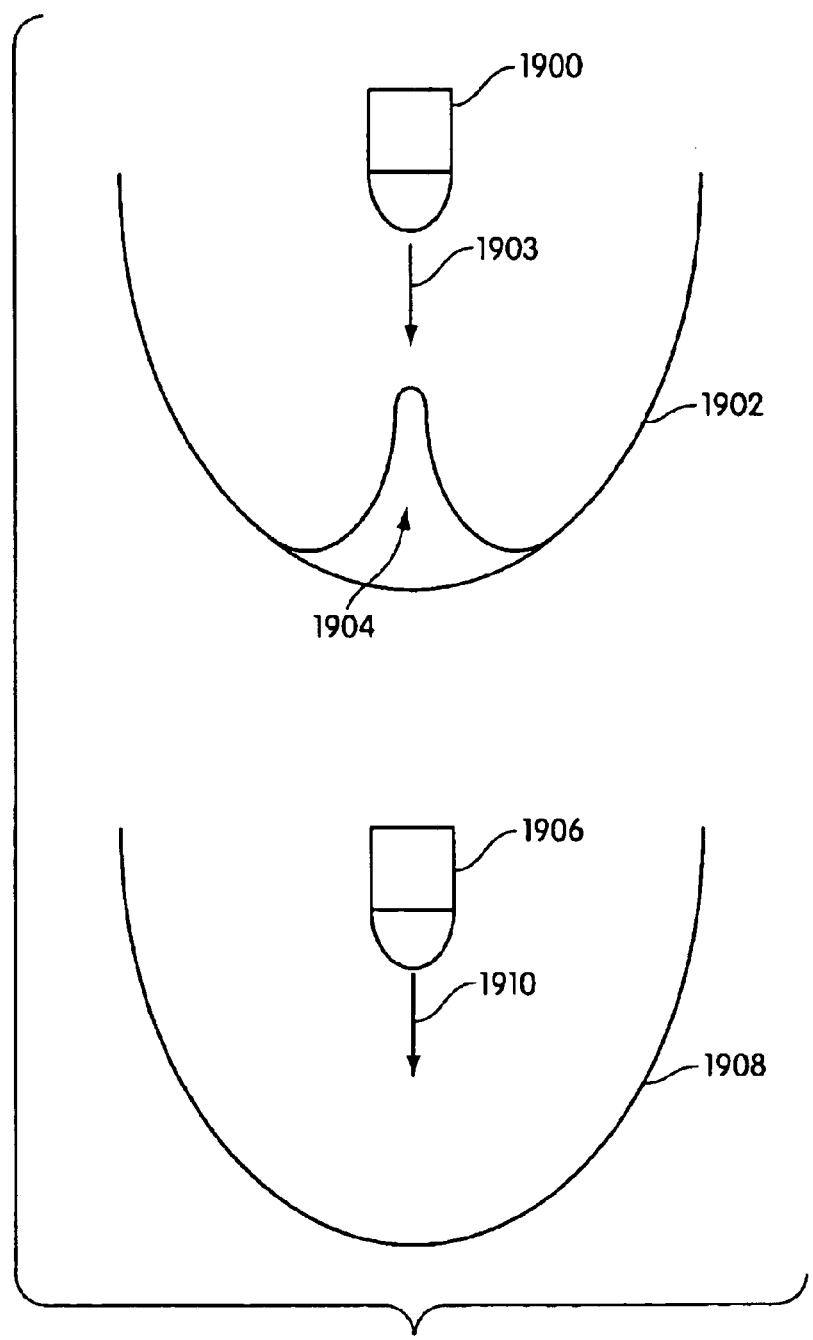
FIG. 19 shows a light and reflector arrangement according to the principles of the invention.
Figure 20:
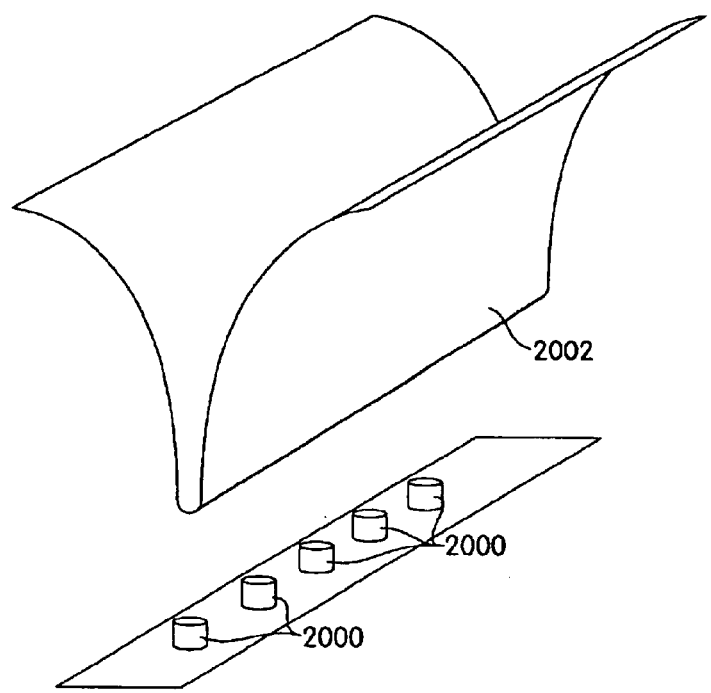
FIG. 20 shows a light and reflector arrangement according to the principles of the invention.
Figure 21:
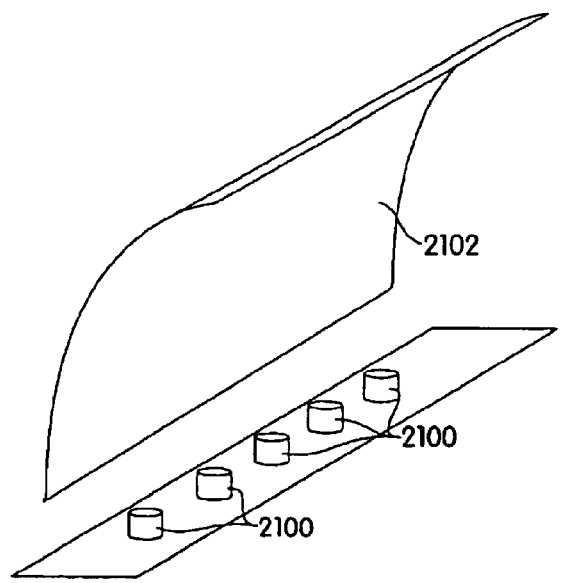
FIG. 21 shows a light and reflector arrangement according to the principles of the invention.

FIG. 19 illustrates a reflector design where an LED 1900 is directed toward a generally parabolic reflector 1902, as indicated by an arrow 1903. The generally parabolic reflector 1902 may include a raised center portion 1904 to further focus or redirect radiation from the LED 1900. As shown by a second LED 1906, a second generally parabolic reflector 1908, and a second arrow 1910, the raised center portion 1904 may be omitted in some configurations. It will be appreciated that the LED 1900 in this configuration, or in the other configurations described herein using reflective surfaces, may be in any package or without a package. Where no package is provided, the LED may be electrically connected on an n-side and a p-side to provide the power for operation. As shown in FIG. 20, a line of LEDs 2000 may be directed toward a planar reflective surface 2002 that directs the line of LEDs 2000 in two opposite planar directions. As shown in FIG. 21, a line of LEDs 2100 may be directed toward a planar surface 2102 that directs the line of LEDs 2100 in one planar direction.

A system such as that described in reference to FIG. 1 may be incorporated into a toy, such as a ball. Control circuitry, a power supply, and LEDs may be suspended or mounted inside the ball, with all or some of the ball exterior formed of a light-transmissive material that allows LED color-changing effects to be viewed. Separate portions of the exterior may be formed from different types of light-transmissive material, or may be illuminated by different groups of LEDs to provide the exterior of the ball to be illuminated in different manners over different regions of its exterior.

The ball may operate autonomously to generate color-changing effects, or may respond to signals from an activation switch that is associated with control circuit. The activation switch may respond to force, acceleration, temperature, motion, capacitance, proximity, Hall effect or any other stimulus or environmental condition or variable. The ball could include one or more activations switches and the control unit can be pre-programmed to respond to the different switches with different color-changing effects. The ball may respond to an input with a randomly selected color-changing effect, or with one of a predetermined sequence of color-changing effects. If two or more switches are incorporated into the ball, the LEDs may be activated according to individual or combined switch signals. This could be used, for example, to create a ball that has subtle effects when a single switch is activated, and dramatic effects when a plurality of switches are activated.

The ball may respond to transducer signals. For example, one or more velocity or acceleration transducers could detect motion in the ball. Using these transducers, the ball may be programmed to change lighting effects as it spins faster or slower. The ball could also be programmed to produce different lighting effects in response to a varying amount of applied force. There are many other useful transducers, and methods of employing them in a color-changing ball.

The ball may include a transceiver. The ball may generate color-changing effects in response to data received through the transceiver, or may provide control or status information to a network or other devices using the transceiver. Using the transceiver, the ball may be used in a game where several balls communicate with each other, where the ball communicates with other devices, or communicates with a network. The ball could then initiate these other devices or network signals for further control.

A method of playing a game could be defined where the play does not begin until the ball is lighted or lighted to a particular color. The lighting signal could be produced from outside of the playing area by communicating through the transceiver, and play could stop when the ball changes colors or is turned off through similar signals. When the ball passes through a goal the ball could change colors or flash or make other lighting effects. Many other games or effects during a game may be generated where the ball changes color when it moves too fast or it stops. Color-changing effects for play may respond to signals received by the transceiver, respond to switches and/or transducers in the ball, or some combination of these. The game hot potato could be played where the ball continually changes colors, uninterrupted or interrupted by external signals, and when it suddenly or gradually changes to red or some other predefined color you have to throw the ball to another person. The ball could have a detection device such that if the ball is not thrown within the predetermined period it initiates a lighting effect such as a strobe. A ball of the present invention may have various shapes, such as spherical, football-shaped, or shaped like any other game or toy ball.

As will be appreciated from the foregoing examples, an LED system such as that described in reference to FIGS. 1 & 2A–2B may be adapted to a variety of color-changing toys and games. For example, color-changing effects may be usefully incorporated into many games and toys, including a toy gun, a water gun, a toy car, a top, a gyroscope, a dart board, a bicycle, a bicycle wheel, a skateboard, a train set, an electric racing car track, a pool table, a board game, a hot potato game, a shooting light game, a wand, a toy sword, an action figure, a toy truck, a toy boat, sports apparel and equipment, a glow stick, a kaleidoscope, or magnets. Color-changing effects may also be usefully incorporated into branded toys such as a View Master, a Super Ball, a Lite Brite, a Harry Potter wand, or a Tinkerbell wand.

Figure 22:
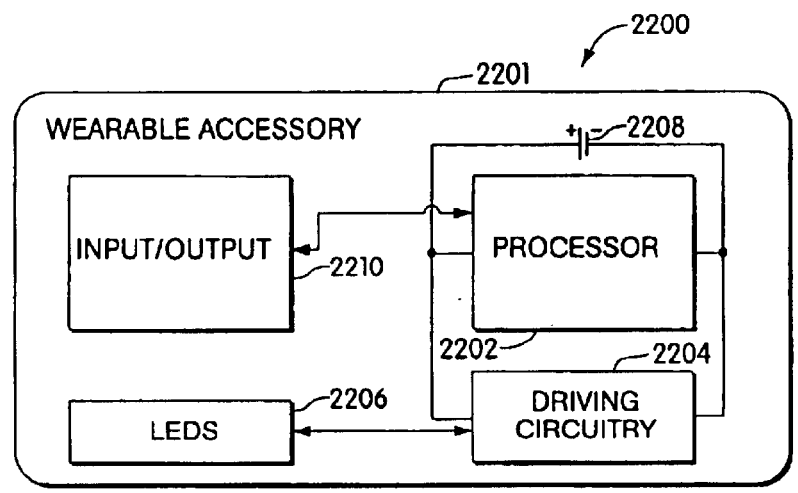
FIG. 22 is a block diagram of an embodiment of a device according to the principles of the invention having internal illumination circuitry.

FIG. 22 is a block diagram of an embodiment of a device according to the principles of the invention having internal illumination circuitry. The device 2200 is a wearable accessory that may include a system such as that described with reference to FIGS. 1 and 2A–2B. The device may have a body 2201 that includes a processor 2202, driving circuitry 2204, one or more LED's 2206, and a power source 2208. The device 2200 may optionally include input/output 2210 that serves as an interface by which programming may be received to control operation of the device 2200. The body 2201 may include a light-transmissive portion that is transparent, translucent, or translucent-diffusing for permitting light from the LEDs 2206 to escape from the body 2200. The LEDs 2206 may be mounted, for example, along an external surface of a suitable diffusing material. The LEDs 2206 may be placed inconspicuously along the edges or back of the diffusing material. Surface mount LED's may be secured directly to the body 2200 on an interior surface of a diffusing material.

The input/output 2210 may include an input device such as a button, dial, slider, switch or any other device described above for providing input signals to the device 2200, or the input/output 2210 may include an interface to a wired connection such as a Universal Serial Bus connection, serial connection, or any other wired connection, or the input/output 2210 may include a transceiver for wireless connections such as infrared or radio frequency transceivers. In an embodiment, the wearable accessory may be configured to communicate with other wearable accessories through the input/output 2210 to produce synchronized lighting effects among a number of accessories. For wireless transmission, the input/output 2210 may communicate with a base transmitter using, for example, infrared or microwave signals to transmit a DMX or similar communication signal. The autonomous accessory would then receive this signal and apply the information in the signal to alter the lighting effect so that the lighting effect could be controlled from the base transmitter location. Using this technique, several accessories may be synchronized from the base transmitter. Information could also then be conveyed between accessories relating to changes of lighting effects. In one instantiation, the input/output 2210 may include a transmitter such as an Abacom TXM series device, which is small and low power and uses the 400 Mhz spectrum. Using such a network, multiple accessories on different people, can be synchronized to provide interesting effects including colors bouncing from person to person or simultaneous and synchronized effects across several people. A number of accessories on the same person may also be synchronized to provide coordinated color-changing effects. A system according to the principle of the invention may be controlled though a network as described herein. The network may be a personal, local, wide area or other network. The Blue Tooth standard may be an appropriate protocol to use when communicating to such systems although any protocol could be used.

The input/output 2210 may include sensors for environmental measurements (temperature, ambient sound or light), physiological data (heart rate, body temperature), or other measurable quantities, and these sensor signals may be used to produce color-changing effects that are functions of these measurements.

A variety of decorative devices can be used to give form to the color and light, including jewelry and clothing. For example, these could take the form of a necklaces, tiaras, ties, hats, brooches, belt-buckles, cuff links, buttons, pins, rings, or bracelets, anklets etc. Some examples of shapes for the body 2201, or the light-transmissive portion of the body, icons, logos, branded images, characters, and symbols (such as ampersands, dollar signs, and musical notes). As noted elsewhere, the system may also be adapted to other applications such as lighted plaques or tombstone signs that may or may not be wearable.

Figure 23:
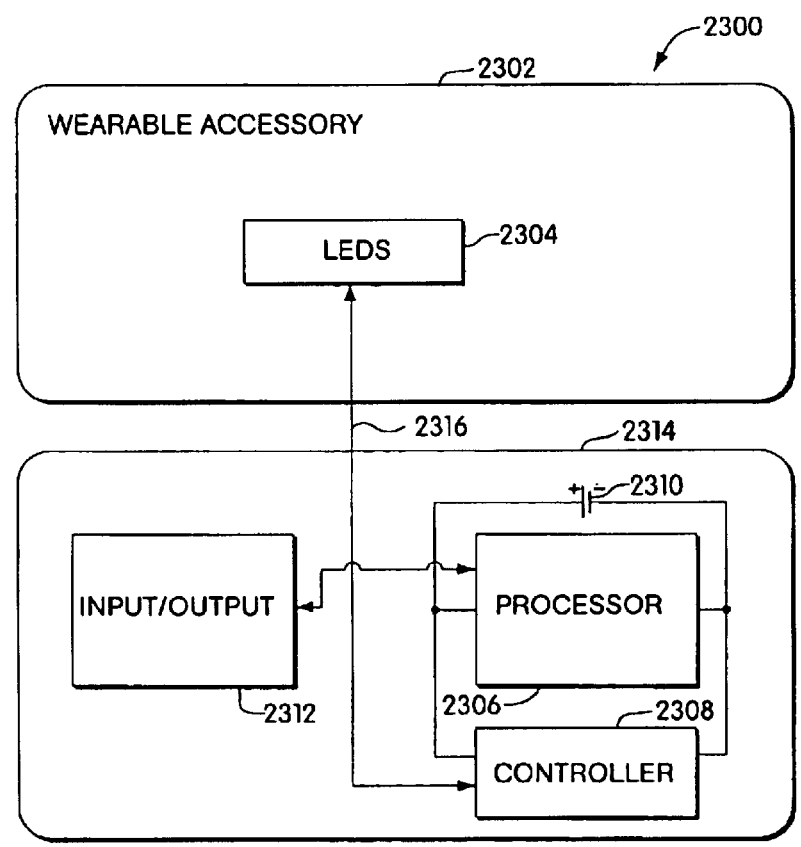
FIG. 23 is a block diagram of an embodiment of a device according to the principles of the invention having external illumination circuitry.

FIG. 23 is a schematic diagram of an embodiment of a device according to the principles of the invention having external illumination circuitry. As shown in FIG. 23, a wearable accessory 2300 may include a first housing 2302 such as a wearable accessory that includes one or more LED's 2304. Illumination circuitry including a processor 2306, controllers 2308, a power source 2310, and an input/output 2312 are external to the first housing 2302 and may be included in a second housing 2314. A link 2316 is provided so that the illumination circuitry may communicated drive signals to the LEDs 2304 within the first housing 2302. This configuration may be convenient for applications where the first housing 2302 is a small accessory or other wearable accessory that may be connected to remote circuitry, as in, for example, the buttons of a shirt. It will be appreciated that while all of the illumination circuitry except for the LEDs 2304 are shown as external to the first housing 2302, one or more of the components may be included within the first housing 2302.

Figure 24:
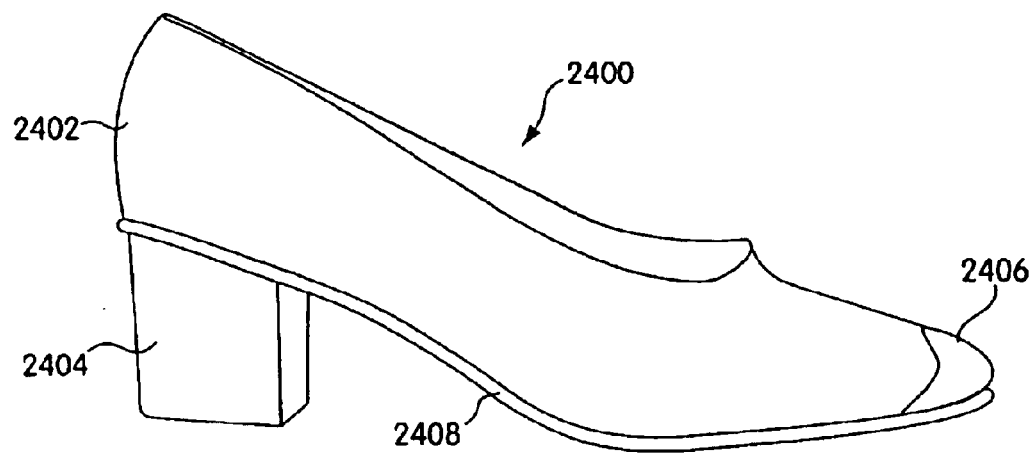
FIG. 24 depicts an autonomous color-changing shoe according to the principles of the invention.

FIG. 24 depicts an autonomous color-changing shoe according to the principles of the invention. A shoe 2400 includes a main portion 2402, a heel 2404, a toe 2406, and a sole 2408. The main portion 2402 is adapted to receive a human foot, and may be fashioned of any material suitable for use in a shoe. The heel 2402 may be formed of a translucent, diffusing material, and may have embedded therein a system such as that described with reference to FIGS. 1 and 2A–2B. In addition to, or instead of a heel 2402 with autonomous color changing ability, another portion of the shoe 2400 may include an autonomous color changing system, such as the toe 2406, the sole 2408, or any other portion. A pair of shoes may be provided, each including an input/output system so that the two shoes may communicate with one another to achieve synchronized color changing effects. In an embodiment of the shoe 2400, circuitry may be placed within a sole 2408 of the shoe, with wires for driving LED's that are located within the heel 2404 or the toe 2406, or both.

As will be appreciated from the foregoing example, the systems disclosed herein may have wide application to a variety of wearable and ornamental objects. Apparel employing the systems may include coats, shirts, pants, clothing, shoes, footwear, athletic wear, accessories, jewelry, backpacks, dresses, hats, bracelets, umbrellas, pet collars, luggage, and luggage tags. Ornamental objects employing the systems disclosed herein may include picture frames, paper weights, gift cards, bows, and gift packages.

Color-changing badges and other apparel may have particular effect in certain environments. The badge, for example, can be provided with a translucent, semi-translucent or other material and one or more LEDs can be arranged to provide illumination of the material. In a one embodiment, the badge would contain at least one red, one blue and one green LED and the LEDs would be arranged to edge light the material. The material may have a pattern such that the pattern reflects the light. The pattern may be etched into the material such that the pattern reflects the light traveling through the material and the pattern appears to glow. When the three colors of LEDs are provided, many color changing effects can be created. This may create an eye-catching effect and can bring attention to a person wearing the badge, a useful attention-getter in a retail environment, at a trade show, when selling goods or services, or in any other situation where drawing attention to one's self may be useful.

The principle of edge lighting a badge to illuminate etched patterns can be applied to other devices as well, such as an edge lit sign. A row of LEDs may be aligned to edge light a material and the material may have a pattern. The material may be lit on one or more sides and reflective material may be used on the opposing edges to prevent the light from escaping at the edges. The reflective material also tends to even the surface illumination. These devices can also be backlit or lit through the material in lieu of, or in addition to, edge lighting.

Figure 25:
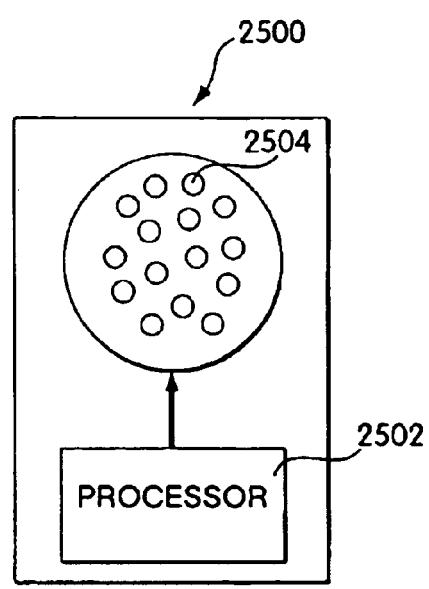
FIG. 25 depicts a device for use with color-changing icicles.

FIG. 25 depicts an LED device according to the invention. The device 2500 may include a processor 2502 and one or more LEDs 2504 in a configuration such as that described in 18 reference to FIGS. 1 and 2A–2B. The device 2500 may be adapted for use with icicles formed from light-transmissive material. The icicles may be mock icicles formed from plastic, glass, or some other material, and may be rendered in a highly realistic, detailed fashion, or in a highly stylized, abstract fashion. A number of color-changing icicles are described below.

Figure 26:
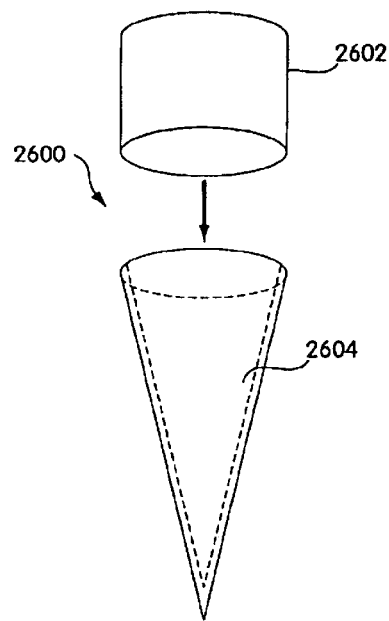
FIGS. 26–30 depict color-changing icicles.

FIG. 26 illustrates a lighted icicle 2600, where an LED lighting device 2602 such as that described in FIGS. 1, 2A–2B, and 25 is used to provide the illumination for an icicle 2604. The icicle 2604 could be formed from a material such as a semi-transparent material, a semi-translucent material, a transparent material, plastic, paper, glass, ice, a frozen liquid or any other material suitable for forming into an icicle and propagating LED radiation. The icicle 2604 may be hollow, or may be a solid formed from light-transmissive material. The illumination from the lighting device 2602 is directed at the icicle 2604 and couples with the icicle 2604. The icicle material may have imperfections to provide various lighting effects. One such effect is created when a primarily transparent material contains a pattern of defects. The defects may redirect the light passing through or along the material, causing bright spots or areas to appear in the illuminated material. If these imperfections are set in a pattern, the pattern will appear bright while the other areas will not appear lighted. The imperfections can also substantially cover the surface of the icicle 2604 to produce a frosted appearance. Imperfections that substantially uniformly cover the surface of the icicle 2604 may create an effect of a uniformly illuminated icicle.

The icicle 2604 can be lit with one or more LEDs to provide illumination. Where one LED is used, the icicle 2604 may be lit with a single color with varying intensity or the intensity may be fixed. In one embodiment, the lighted icicle 2600 includes more than one LED and in another embodiment the LEDs are different colors. By providing a lighted icicle 2600 with different colored LEDs, the hue, saturation and brightness of the lighted icicle 2600 can be changed. The two or more LEDs can be used to provide additive color. If two LEDs were used in the lighted icicle 2600 with circuitry to turn each color on or off, four colors could be produced including black when neither LED is energized. Where three LEDs are used in the lighted icicle 2600 and each LED has three intensity settings, $3^3$ or 27 color selections are available. In one embodiment, the LED control signals would be PWM signals with eight bits (=128 combinations) of resolution. Using three different colored LEDs, this provides $128^3$ or 16.7 million available colors.

Figure 27:
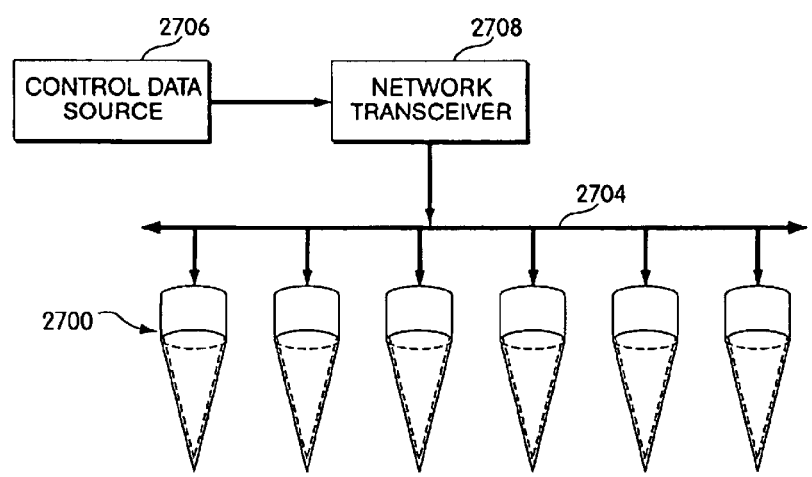

FIG. 27 illustrates a plurality of icicles sharing a network. A plurality of lighted icicles 2700 each include a network interface to communicate over a network 2702, such as any of the networks mentioned above. The network 2704 may provide lighting control signals to each of the plurality of lighted icicles 2700, each of which may be uniquely addressable. Where the lighted icicles 2700 are not uniquely addressable, control information may be broadcast to all of the lighted icicles 2700. A control data source 2706, such as a computer or any of the other controls mentioned above, may provide control information to the lighted icicles 2700 through a network transceiver 2708 and the network 2704. One of the lighted icicles 2700 could also operate as a master icicle, providing control information to the other lighted icicles 2700, which would be slave icicles. The network 2704 may be used generally to generate coordinated or uncoordinated color-changing lighting effects from the plurality of lighted icicles.

One or more of the plurality of lighted icicles 2700 may also operate in a stand-alone mode, and generate color-changing effects separate from the other lighted icicles 2700. The lighted icicles 2700 could be programmed, over the network 2704, for example, with a plurality of lighting control routines to be selected by the user such as different solid colors, slowly changing colors, fast changing colors, stobing light, or any other lighting routines. The selector switch could be used to select the program. Another method of selecting a program would be to turn the power to the icicle off and then back on within a predetermined period of time. For example, non-volatile memory could be used to provide an icicle that remembers the last program it was running prior to the power being shut off. A capacitor could be used to keep a signal line high for 10 seconds and if the power is cycled within this period, the system could be programmed to skip to the next program. If the power cycle takes more then 10 seconds, the capacitor discharges below the high signal level and the previous program is recalled upon re-energizing the system. Other methods of cycling through programs or modes of operation are known, and may be suitably adapted to the systems described herein.

Figure 28:
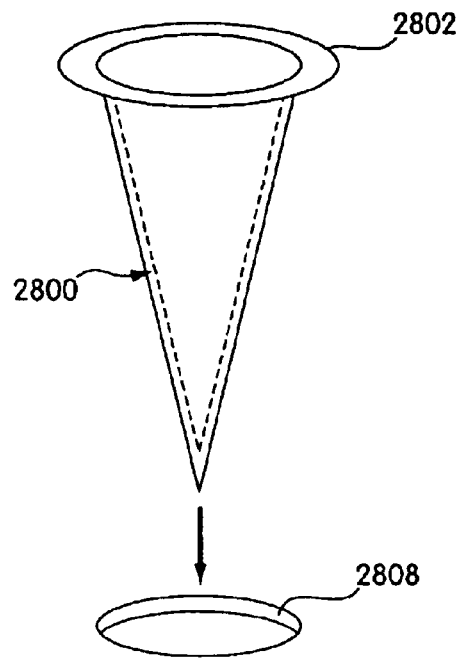

FIG. 28 depicts an icicle 2800 having a flange 2802. The flange 2802 may allow easy mounting of the icicle 2800. In one embodiment, the flange 2802 is used such that the flange couples with a ledge 2808 while the remaining portion of the icicle 2800 hangs through a hole formed by the ledge 2808. This method of attachment is useful where the icicles can hang through existing holes or holes can be made in the area where the icicles 2800 are to be displayed. Other attachment methods are known, and may be adapted to use with the invention.

Figure 29:
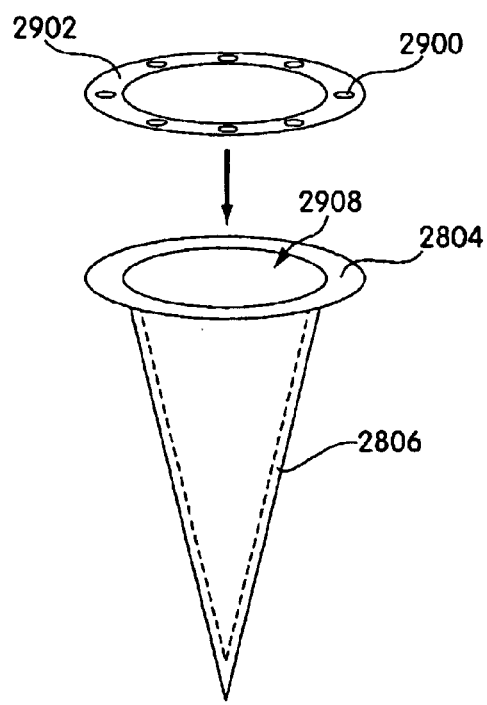

FIG. 29 shows an icicle according to the principles of the invention. A plurality of LEDs 2900 may be disposed in a ring 2902. The ring 2902 may be engaged to a flange 2904 of an icicle 2906. Arranged in this manner, the LEDs 2900 may radiate illumination that is transmitted through icicle 2906. If the ring 2902 is shaped and sized so that the LEDs 2900 directly couple to the flange 2904, then the icicle 2906 will be edge-lit. The ring 2902 may instead be smaller in diameter than the flange 2904, so that the LEDs 2900 radiate into a hollow cavity 2908 in the icicle 2906, or onto a top surface of the icicle 2906 if the icicle 2906 is formed of a solid material.

Figure 30:
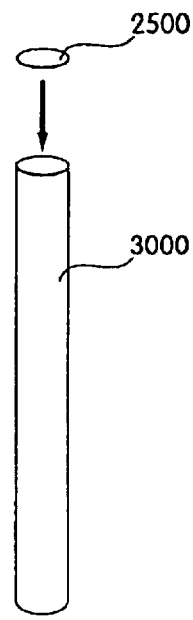

FIG. 30 depicts a solid icicle 3000 which may be in the form or a rod or any other suitable form, with one or more LEDs 3002 positioned to project light into the solid icicle 3000.

Figure 31:
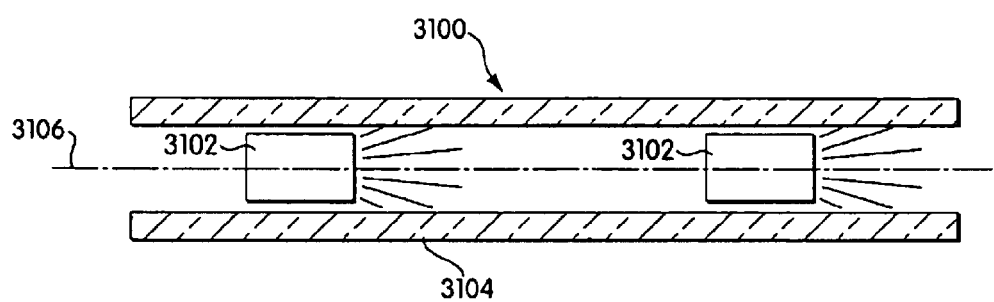
FIG. 31 depicts a color-changing rope light.

FIG. 31 depicts a rope light according to the principles of the invention. The rope light 3100 may include a plurality of LEDs or LED subsystems 3102 according to the description provided in reference to FIGS. 1 and 2A–2B. In one embodiment, three LED dies of different colors may be packaged together in each LED subsystem 3102, with each die individually controllable. A plurality of these LED subsystems 3102 may be disposed inside of a tube 3102 that is flexible and semi-transparent. The LED subsystems 3102 may be spaced along the tube 3104, for example, at even intervals of every six inches, and directed along an axis 3106 of the tube 3104. The LED subsystems 3102 may be controlled through any of the systems and methods described above. In one embodiment, a number of LED subsystems 3102 may be controlled by a common signal, so that a length of tube 3104 of several feet or more may appear to change color at once. The tube 3104 may be fashioned to resemble a rope, or other cylindrical material or object. The LED subsystems 3102 may be disposed within the tube 3104 in rings or other geometric or asymmetric patterns. The LED subsystems 3102 could also be aligned to edge light the tube 3104, as described above. A filter or film may be provided on an exterior surface or an interior surface of the tube 3104 to create pleasing visual effects.

Other consumer products may be realized using the systems and methods described herein. A hammer may generate color-changing effects in response to striking a nail; a kitchen timer may generate color-changing effects in response to a time countdown, a pen may generate color-changing effects in response to the act of writing therewith, or an electric can opener may generate color-changing effects when activated. While the invention has been disclosed in connection with the preferred embodiments shown and described in detail, various modifications and improvements thereon will become readily apparent to those skilled in the art. Accordingly, the spirit and scope of the present invention is to be limited only by the following claims.

We claim:

1. A device comprising:
   a plurality of LEDs configured to produce light that includes at least two different spectra;
   a material configured to receive the light emitted from the plurality of LEDs, and to display a color that is a combination of the at least two different spectra;
   a processor configured to generate at least one control signal to control power delivered to one or more of the plurality of LEDs, the processor further configured to change the at least one control signal over time so as to produce from the device at least one dynamic lighting effect; and
   a user interface adapted to receive a user input to control operation of the processor so as to facilitate a change in the color that is the combination of the at least two different spectra.

2. The device of claim 1 wherein the processor is configured to operate in one of a plurality of modes, each mode producing at least one dynamic lighting effect according to one or more parameters.

3. The device of claim 1 wherein the user interface consists of a single button.

4. The device of claim 1 wherein the user interface consists of two buttons.

5. The device of claim 1 wherein the user interface includes an adjustable input.

6. The device of claim 1 wherein the user interface includes at least one of a button, a dial, a slider, a knob, or a keypad.

7. The device of claim 1 wherein the at least one dynamic lighting effect comprises at least one color-changing effect including at least one of a color wash, a strobe, a fade, or a Holiday lighting effect.

8. The device of claim 1 wherein the device is configured as a consumer product.

9. The device of claim 1, wherein the device is configured as a replacement lighting device to engage mechanically and electrically with a conventional power adapter or socket.

10. The device of claim 1, wherein the device is configured as a light bulb.

11. The device of claim 1, wherein the device is configured as a landscape lighting device.

12. The device of claim 1, wherein the device is configured as a night light.

13. The device of claim 1, wherein the device is configured as a rope light.

14. The device of claim 1, wherein the device is configured as a household product.

15. The device of claim 1, wherein the device is configured as a pen.

16. The device of claim 1, wherein the device is configured to form at least part of a consumer electronic device.

17. The device of claim 1, wherein the device is configured as a glow stick.

18. The device of claim 1, wherein the device is configured as an ornamental or decorative lighting device.

19. The device of claim 18, wherein the device is configured as at least one icicle-shaped lighting device.

20. The device of claim 1, wherein the device is configured to form at least part of a toy or game.

21. The device of claim 20, wherein the toy is constructed and arranged as a lighted ball.

22. The lighted ball of claim 21, further comprising a ball housing, wherein:
at least a portion of the ball housing includes the material; and
the plurality of LEDs are arranged to illuminate the portion of the ball housing including the material.

23. The lighted ball of claim 22, further comprising:
at least one switch associated with the processor, wherein the at least one switch comprises at least one of a Hall effect switch, a motion sensing switch, a proximity detector, a sensor, a transducer, a capacitive switch, and an inductive switch,
wherein the processor is configured to be responsive to the at least one switch so as to generate the at least one control signal.

24. The device of claim 1, wherein the device is configured to form at least part of a wearable accessory.

25. The device of claim 24, wherein:
the device is at least partially enclosed in at least one housing;
at least a portion of the housing includes the material; and
the housing is formed as at least one of a piece of jewelery, a badge, a shoe, a sneaker, an article of clothing, a hat, and an ornamental device.

26. The device of claim 25, wherein the material includes an at least partially light-transmissive material having at least one of a pattern, an etched surface, and an image thereon.

27. The device of claim 25, the material is formed into a shape of at least one of an icon, a logo, a branded image, a character, and a symbol.

28. The device of claim 1, further including at least one support for the plurality of LEDs, wherein the material is arranged with respect to the at least one support such that the light generated by the plurality of LEDs illuminates the material.

29. The device of claim 1, further including at least one sensor to monitor at least one detectable condition, wherein the processor is configured to generate the at least one control signal in response to the at least one detectable condition.

30. The device of claim 1, wherein the processor is configured to receive information from a network and process the information so as to generate the at least one control signal.

31. The device of claim 1, further including at least one timing device, wherein the processor is configured to respond to the at least one timing device so as to generate timed dynamic lighting effects.

32. The device of claim 31, wherein the at least one timing device includes a calendar, and wherein the processor is configured to respond to the calendar so as to generate seasonal dynamic lighting effects.

33. The device of claim 1, wherein the material comprises at least one of a semi-transparent material, a translucent material, a light-diffusing material and a transparent material.

34. The device of claim 33, wherein the material includes a pattern of defects configured to redirect the light passing through or along the material.

35. The device of claim 33, further comprising a housing, wherein the plurality of LEDs and the processor are supported by the housing, and wherein the material forms at least a portion of the housing.

36. The device of claim 35, wherein the housing is configured such that the plurality of LEDs and the processor are substantially enclosed by the housing.

37. The device of claim 35, wherein the user interface is integrated into the housing.

38. The device of claim 33, further comprising:
a first housing portion that substantially encloses at least the processor; and
a second housing portion, coupled to the first housing portion, that substantially encloses the at least two LEDs, wherein the material forms at least a portion of the second housing portion.

39. The device of claim 38, wherein the first housing portion includes a battery case configured to contain at least one battery to provide power to the device.

40. The device of claim 1, further comprising at least one optic.

41. The device of claim 40, wherein the at least one optic includes at least one detachable optic.

42. The device of claim 40, wherein the at least one optic includes one of a reflector, a diffuser, a filter, a lens, a secondary optic, a holographic lens, an anamorphic lens, and a patterned lens.

43. The device of claim 1, further comprising a power converter to provide power for at least one of the processor and the plurality of LEDs.

44. The device of claim 1, further comprising a power connection adapted to engage mechanically and electrically with a conventional light socket.

45. The device of claim 44, wherein the power connection includes at least one of a plug, a bi-pin base, and a screw base.

46. The device of claim 44, wherein:
the power connection includes a base adapted to engage mechanically and electrically with a conventional three-way socket; and
the user interface includes a switch of the conventional three-way socket,
wherein the processor is configured to generate the at least one control signal based at least in part on a setting of the switch of the conventional three-way socket.

47. The device of claim 1, wherein the processor is configured to monitor a power supply signal to the device and to generate the at least one control signal based at least in part on the monitored power supply signal.

48. The device of claim 47, wherein the user interface is configured to control at least power to the device.

49. The device of claim 48, wherein the user interface includes a conventional AC dimmer control to vary the power supply signal to the device, and wherein the processor generates the at least one control signal in response to operation of the conventional AC dimmer control.

50. The device of claim 49, wherein the processor is configured to produce from the device the at least one dynamic lighting effect in response to operation of the conventional AC dimmer control, including at least one of a dimming effect, a color-changing effect, and a light pattern effect.

51. The device of claim 1, wherein the user interface is configured to allow a user to do at least one of the following:
select a desired lighting program stored in the memory for execution by the processor; and
modify the execution of at least one lighting program.

52. The device of claim 51, wherein at least one lighting program includes at least one adjustable parameter and is arranged to cause the device to produce the at least one dynamic lighting effect according to the at least one adjustable parameter when executed by the processor, and wherein:

the user interface is configured to allow the user to adjust the at least one adjustable parameter of the at least one lighting program.

53. The device of claim 51, wherein the user interface is adapted to output at least one of a logic high signal and logic low signal to the processor, and wherein the processor is configured to select at least one lighting program from the memory upon receipt of the signal output by the user interface.

54. The device of claim 51, wherein the user interface is adapted to output at least one of a logic high signal and logic low signal to the processor, and wherein the processor is configured to adjust at least one parameter of the at least one lighting program upon receipt of the signal output by the user interface.

55. The device of claim 51, wherein the processor is adapted to measure a duration of a signal output by the user interface, and wherein the processor is configured to adjust at least one parameter of the at least one lighting program upon receipt of a signal output by the user interface having a predetermined duration.

56. The device of claim 55, wherein the processor is configured to continually change the at least one parameter until the signal output by the user interface changes.

57. The device of claim 51, further comprising an analog to digital converter, wherein:

the user interface is configured to generate an analog signal;

the analog to digital converter is arranged to convert the analog signal to a digital signal; and the processor is configured to generate the at least one control signal in response to the digital signal.

58. The device of claim 51, further comprising a housing, wherein the plurality of LEDs and the processor are supported by the housing, wherein the user interface is integrated with the housing, and wherein the material forms at least a portion of the housing.

59. The device of claim 58, wherein the at least one user interface includes at least one of a button, a dial, a slider, a knob, a switch, a variable switch, a variable selector, a keypad, a thumbwheel and a rotatable dial that forms a collar around the housing.

60. The device of claim 51, wherein the user interface is located remotely from the processor.

61. The device of claim 60, wherein the user interface and the processor are configured to communicate via at least one of an electromagnetic transmission, a radio frequency transmission, an infrared transmission, a microwave transmission, an acoustic transmission, a wire transmission, a cable transmission, and a network transmission.

62. The device of claim 51, further comprising at least one controller coupled to the processor and configured to control the plurality of LEDs in response to the at least one control signal, the controller including at least one of a pulse width modulator, a pulse amplitude modulator, a pulse displacement modulator, a resistor ladder, a current source, a voltage source, a voltage ladder, a switch, a transistor, and a voltage controller.

63. The device of claim 51, further comprising a display associated with the processor.

64. The device of claim 63, wherein the display includes at least one of an LCD screen, a plasma screen, a monochrome screen, a black and white screen and a color screen.

65. The device of claim 63, wherein the display is adapted to display information regarding at least one of: at least one lighting program; at least one setting of at least one lighting program; at least one parameter of at least one lighting program; available lighting programs; a time; a date; and control information.

66. The device of claim 51, wherein:

the processor is configured to monitor power to the device and to generate the at least one control signal based at least in part on the monitored power; and the user interface is configured to control at least the power to the device.

67. The device of claim 66, wherein the processor is configured to select a different lighting program from the memory if the monitored power includes a power cycle having less than a predetermined duration.

68. The device of claim 67, wherein the memory includes at least one of a non-volatile memory and a battery-backed memory, and wherein the processor is configured to select from the memory a last executed lighting program if the monitored power includes a power cycle having greater than the predetermined duration.

69. In a device comprising a plurality of LEDs configured to produce light that includes at least two different spectra, a memory to store at least one lighting program and a material configured to receive the light emitted from the plurality of LEDs and display a color that is a combination of the at least two different spectra, a method comprising an act of:

A) controlling a power delivered to one or more of the plurality of LEDs over time, in response to a user input and execution of the at least one lighting program, so as to produce at least one dynamic lighting effect determined substantially by the at least one lighting program; and A1) varying the user input so as to facilitate a change in the color that is the combination of the at least two different spectra.

70. The method of claim 69, wherein the method further comprises an act of:

selecting one mode of a plurality of modes in response to the user input, each mode configured to produce at least one dynamic lighting effect according to one or more parameters; and performing the act A) based at least in part on the selected one mode.

71. The method of claim 70, wherein the method further comprises acts of:

adjusting the one or more parameters of the selected one mode in response to the user input; and performing the act A) based at least in part on the adjusted one or more parameters.

72. The method of claim 69, further comprising an act of:

B) providing the user input via only a single user operated device.

73. The method of claim 72, wherein the single user operated device includes a single button, and wherein the act B) comprises an act of:

providing the user input via only the single button.

74. The method of claim 69, further comprising an act of:

providing the user input via only two user operated buttons.

75. The method of claim 69, further comprising an act of:

providing the user input via at least one adjustable user operated device so as to provide at least one adjustable user input.

76. The method of claim 69, further comprising an act of:
providing the user input via at least one of a button, a dial, a slider, a knob, a switch, a variable switch, a variable selector, a keypad, a thumbwheel and a rotatable dial that forms a collar around the device.

77. The method of claim 69, wherein the at least one dynamic lighting effect comprises at least one color-changing effect including at least one of a color wash, a strobe, a fade, or a Holiday lighting effect, and wherein the act A) comprises an act of:
controlling the power delivered to the one or more LEDs, in response to the user input, so as to produce at least one of the color wash, the strobe, the fade, or the Holiday lighting effect.

78. The method of claim 69, further comprising acts of:
monitoring at least one detectable condition; and
performing the act A) based at least in part on the at least one detectable condition and the user input.

79. The method of claim 78, wherein the at least one detectable condition includes at least one environmental condition, and wherein the method comprises acts of:
monitoring the at least one environmental condition; and
performing the act A) based at least in part on the at least one environmental condition and the user input.

80. The method of claim 69, further comprising acts of:
receiving information from a network; and
processing the information so as to perform the act A).

81. The method of claim 69, wherein the device further includes at least one timing device, and wherein the method further comprises an act of:
B) performing the act A) in response to the at least one timing device and the user input so as to generate timed dynamic lighting effects.

82. The method of claim 81, wherein the at least one timing device includes a calendar, and wherein the act B) comprises an act of:
performing the act A) in response to the calendar and the user input so as to generate seasonal dynamic lighting effects.

83. The method of claim 69, further comprising acts of:
monitoring a power supply signal to the device; and
performing the act A) based at least in part on the monitored power supply signal.

84. The method of claim 83, further comprising an act of:
B) controlling at least power to the device via a user interface to provide the user input.

85. The method of claim 84, wherein the user interface includes a conventional AC dimmer control, and wherein the act B) comprises acts of:
varying the power supply signal to the device via the conventional AC dimmer control; and
performing the act A) in response to user operation of the conventional AC dimmer control.

86. The method of claim 85, wherein the act A) comprises an act of:
producing from the device the at least one dynamic lighting effect in response to operation of the conventional AC dimmer control, including at least one of a dimming effect, a color-changing effect, and a light pattern effect.

87. The method of claim 69, wherein the device further comprises a power connection adapted to engage mechanically and electrically with a conventional light socket, and wherein the method further comprises an act of:
providing the user input via at least one user interface that controls at least power provided to the conventional light socket.

88. The method of claim 87, wherein the power connection includes at least one of a plug, a bi-pin base, and a screw base.

89. The method of claim 87, wherein:
the power connection is adapted to engage mechanically and electrically with a conventional three-way socket; and
the at least one user interface includes a switch of the conventional three-way socket,
wherein the act A) comprises an act of:
controlling at least the power delivered to one or more of the plurality of LEDS based at least in part on a setting of the switch of the conventional three-way socket.

90. The method of claim 69, wherein the act A) comprises an act of performing one of the following acts in response to the user input:
C1) selecting a desired lighting program stored in the memory for execution; and
C2) modifying the execution of the at least one lighting program.

91. The method of claim 90, wherein the at least one lighting program includes at least one adjustable parameter, wherein the at least one lighting program is arranged to cause the device to produce the at least one dynamic lighting effect according to the at least one adjustable parameter when executed, and wherein the act C2) comprises an act of:
adjusting the at least one adjustable parameter of the at least one lighting program via the user input.

92. The method of claim 90, wherein the user input includes at least one of a logic high signal and logic low signal, and wherein the act C1) comprises an act of:
selecting the desired lighting program from the memory in response to the at least one of the logic high signal and the logic low signal.

93. The method of claim 90, wherein the user input includes at least one of a logic high signal and logic low signal, and wherein the act C2) comprises an act of:
adjusting at least one parameter of the at least one lighting program in response to the at least one of the logic high signal and the logic low signal.

94. The method of claim 90, further comprising an act of:
measuring a duration of the user input.
wherein the act C2) comprises an act of adjusting at least one parameter of the at least one lighting program based on a predetermined duration of the user input.

95. The method of claim 94, wherein the act C2) comprises an act of continually changing the at least one parameter until the user input changes.

96. The method of claim 90, further comprising acts of:
providing the user input as an analog signal;
converting the analog signal to a digital signal; and
performing the act A) in response to the digital signal.

97. The method of claim 90, further comprising an act of:
D) providing the user input remotely from the device.

98. The method of claim 97, wherein the act D) comprises an act of:
providing the user input via at least one of an electromagnetic transmission, a radio frequency transmission, an infrared transmission, a microwave transmission, an acoustic transmission, a wire transmission, a cable transmission, and a network transmission.

99. The method of claim 90, wherein the act A) comprises an act of:
controlling the power to the one or more LEDs using at least one of a pulse width modulator, a pulse amplitude modulator, a pulse displacement modulator, a resistor ladder, a current source, a voltage source, a voltage ladder, a switch, a transistor, and a voltage controller.

100. The method of claim 90, wherein the device further comprises a display, and wherein the method further comprises an act of:

displaying information on the display regarding at least one of: at least one lighting program; at least one setting of at least one lighting program; at least one parameter of at least one lighting program; available lighting programs; a time; a date; and control information.

101. The method of claim 90, further comprising acts of:

monitoring power to the device;

performing the act A) based at least in part on the monitored power; and controlling the power to the device via the user input.

102. The method of claim 101, further comprising an act of:

selecting a different lighting program from the memory if the monitored power includes a power cycle having less than a predetermined duration.

103. The method of claim 102, wherein the memory includes at least one of a non-volatile memory and a battery-backed memory, and wherein the act of selecting a different lighting program includes an act of selecting from the memory a last executed lighting program if the monitored power includes a power cycle having greater than the predetermined duration.

104. The device of claim 1, wherein the processor is configured to automatically change the at least one control signal over time upon the device being turned on.

* * * * *